(12) United States Patent
Adams et al.

(10) Patent No.: US 8,157,751 B2
(45) Date of Patent: Apr. 17, 2012

(54) COIL MEMBER FOR A MEDICAL DEVICE

(75) Inventors: Mark L. Adams, Sandy, UT (US); Clay W. Northrop, Salt Lake City, UT (US); Ted W. Layman, Park City, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 886 days.

(21) Appl. No.: 11/956,147

(22) Filed: Dec. 13, 2007

(65) Prior Publication Data

US 2009/0156999 A1 Jun. 18, 2009

(51) Int. Cl.
*A61B 5/00* (2006.01)
*A61M 25/00* (2006.01)

(52) U.S. Cl. .................. 600/585; 604/526

(58) Field of Classification Search .............. 600/585; 604/103.09, 526; 623/1.13–1.15, 1.22
See application file for complete search history.

(56) References Cited

U.S. PATENT DOCUMENTS

| | | | |
|---|---|---|---|
| 3,547,103 A | 12/1970 | Cook | |
| 4,465,482 A * | 8/1984 | Tittel | 604/523 |
| 4,733,665 A * | 3/1988 | Palmaz | 606/108 |
| 4,760,845 A | 8/1988 | Kovalcheck | |
| 4,776,337 A * | 10/1988 | Palmaz | 623/1.11 |
| 4,893,623 A * | 1/1990 | Rosenbluth | 606/192 |
| 4,998,923 A * | 3/1991 | Samson et al. | 606/194 |
| 5,040,543 A | 8/1991 | Badera et al. | |
| 5,102,417 A * | 4/1992 | Palmaz | 606/195 |
| 5,125,395 A | 6/1992 | Adair | |
| 5,139,480 A * | 8/1992 | Hickle et al. | 604/8 |
| 5,195,984 A * | 3/1993 | Schatz | 623/1.2 |
| 5,238,004 A | 8/1993 | Sahatjian et al. | |
| 5,437,288 A | 8/1995 | Schwartz et al. | |
| 5,507,751 A * | 4/1996 | Goode et al. | 606/108 |
| 5,514,154 A * | 5/1996 | Lau et al. | 623/1.15 |
| 5,573,520 A * | 11/1996 | Schwartz et al. | 604/526 |
| 5,693,085 A * | 12/1997 | Buirge et al. | 623/1.13 |
| 5,733,303 A * | 3/1998 | Israel et al. | 623/1.15 |
| 5,741,429 A * | 4/1998 | Donadio et al. | 216/8 |
| 5,755,776 A * | 5/1998 | Al-Saadon | 623/1.15 |
| 5,833,632 A | 11/1998 | Jacobsen et al. | |
| 5,868,782 A * | 2/1999 | Frantzen | 623/1.15 |
| 5,931,830 A | 8/1999 | Jacobsen et al. | |
| 5,948,016 A * | 9/1999 | Jang | 623/1.11 |
| 6,001,068 A | 12/1999 | Uchino et al. | |
| 6,001,123 A * | 12/1999 | Lau | 623/1.12 |
| 6,022,343 A | 2/2000 | Johnson et al. | |
| 6,027,863 A | 2/2000 | Donadio, III | |

(Continued)

FOREIGN PATENT DOCUMENTS

EP 0778038 B1 6/2006
(Continued)

*Primary Examiner* — Max Hindenburg
*Assistant Examiner* — Sean Dougherty
(74) *Attorney, Agent, or Firm* — Seager, Tufte & Wickhem, LLC

(57) ABSTRACT

A coil for use in a medical device. The coil includes a plurality of coil windings or turns, wherein adjacent coil windings are connected together at a plurality of discrete connection locations to increase the torsional rigidity and torque transmitting properties of the coil without sacrificing the flexibility characteristics of the coil. In some embodiments the coil may be a wave wound coil, such as a nested wave wound coil or a crest-to-crest wave wound coil.

17 Claims, 33 Drawing Sheets

U.S. PATENT DOCUMENTS

| | | |
|---|---|---|
| 6,179,857 B1 | 1/2001 | Diaz et al. |
| 6,273,876 B1 | 8/2001 | Klima et al. |
| 6,428,570 B1 * | 8/2002 | Globerman ............... 623/1.15 |
| 6,485,440 B1 | 11/2002 | Gardeski |
| 6,551,351 B2 * | 4/2003 | Smith et al. ............... 623/1.16 |
| 6,579,246 B2 | 6/2003 | Jacobsen et al. |
| 6,626,935 B1 * | 9/2003 | Ainsworth et al. ......... 623/1.15 |
| 6,652,548 B2 * | 11/2003 | Evans et al. ............... 606/159 |
| 6,682,493 B2 | 1/2004 | Mirigian |
| 6,766,720 B1 | 7/2004 | Jacobsen et al. |
| 6,907,298 B2 | 6/2005 | Smits et al. |
| 6,921,397 B2 | 7/2005 | Corcoran et al. |
| 7,413,563 B2 * | 8/2008 | Corcoran et al. ........... 604/523 |
| 7,488,338 B2 * | 2/2009 | Eidenschink ............... 606/194 |
| 7,594,927 B2 * | 9/2009 | Majercak et al. ............ 623/1.15 |
| 7,635,384 B2 * | 12/2009 | Gregorich ............... 623/1.15 |
| 7,708,704 B2 * | 5/2010 | Mitelberg et al. ......... 600/585 |
| 7,914,467 B2 * | 3/2011 | Layman et al. ............. 600/585 |
| 2003/0130712 A1 | 7/2003 | Smits et al. |
| 2004/0102720 A1 * | 5/2004 | Kellerman et al. ......... 600/585 |
| 2004/0181174 A2 * | 9/2004 | Davis et al. ............... 600/585 |
| 2005/0054950 A1 | 3/2005 | Parins |
| 2005/0054951 A1 | 3/2005 | Parins |
| 2006/0224231 A1 * | 10/2006 | Gregorich ............... 623/1.16 |
| 2008/0294243 A1 * | 11/2008 | Addonizio et al. ......... 623/1.22 |

FOREIGN PATENT DOCUMENTS

| | | |
|---|---|---|
| WO | 9203964 | 3/1992 |
| WO | 03086523 A1 | 10/2003 |
| WO | 2004091440 | 10/2004 |

* cited by examiner

COIL MEMBER FOR A MEDICAL DEVICE

TECHNICAL FIELD

The disclosure is directed to elongated medical devices. More particularly, the disclosure is directed to coil wound members for a variety of medical devices, such as guidewires, catheters, and the like.

BACKGROUND

A variety of available medical devices, such as guidewires and catheters, have been manufactured which include a flexible metallic tubular member described as a hypotube along at least a portion of the elongate shaft of the medical device. In some cases, a pattern of slots may be formed through the sidewall of a tubular member by cutting or the like. The pattern of slots provides the tubular member with a degree of lateral flexibility while retaining torsional rigidity. However, known manufacturing processes involved in producing such slotted hypotubes are generally complex and/or expensive. Therefore, it is desirable to provide alternative structures and assemblies which provide a desired degree of lateral flexibility while retaining torsional rigidity of a medical device.

SUMMARY

The disclosure is directed to several alternative designs, materials and methods of manufacturing medical device structures and assemblies.

Accordingly, one illustrative embodiment is a medical device coil member comprising a wave wound coil having a first end, a second end and a longitudinal axis extending between the first end and the second end. The wave wound coil is formed of a filament wound about the longitudinal axis forming a plurality of turns, wherein each turn of the filament is a 360 degree revolution of the filament about the longitudinal axis. Each turn of the filament includes a wave pattern. Adjacent turns of the filament are fixed together at two or more discrete locations along the length of the wave wound coil.

Another illustrative embodiment is a medical device coil member comprising a wave wound coil including a plurality of coil windings helically wound about a longitudinal axis of the coil, wherein each coil winding is a 360 degree revolution of a filament of the wave wound coil. The wave wound coil includes a first coil winding, a second coil winding immediately following the first coil winding, a third coil winding immediately following the second coil winding, and a fourth coil winding immediately following the third coil winding. The second coil winding is welded to the first coil winding at two or more discrete locations, the third coil winding is welded to the second coil winding at two or more discrete locations, and the fourth coil winding is welded to the third coil winding at two or more discrete locations.

Yet another illustrative embodiment is a medical device coil member comprising a helically wound coil having a first end, a second end and a longitudinal axis extending between the first end and the second end. The helically wound coil is formed of a filament helically wound about the longitudinal axis, forming a plurality of turns, wherein each turn of the filament is a 360 degree revolution of the filament about the longitudinal axis and each successive turn is spaced from an immediately preceding turn by a gap. Over at least a portion of the length of the coil, each successive turn of the filament may be welded to an immediately preceding turn of the filament at two or more discrete locations by welds extending across the gap between the turns of the filament.

Another illustrative embodiment is a medical device including an elongate shaft. The elongate shaft comprises a wave wound coil extending along a portion of the elongate shaft having a first end, a second end and a longitudinal axis extending between the first end and the second end of the coil. The wave wound coil is formed of a filament wound about the longitudinal axis forming a plurality of turns, wherein each turn of the filament is a 360 degree revolution of the filament about the longitudinal axis. Each turn of the filament includes a wave pattern of two or more high periods and two or more low periods. Each of the plurality of turns of the filament is welded to an immediately preceding turn of the filament at two or more discrete locations along the length of the wave wound coil.

An illustrative method of forming a modified coil for a medical device includes providing a wave wound coil having a first end, a second end and a longitudinal axis extending between the first end and the second end. The wave wound coil is formed of a filament wound about the longitudinal axis forming a plurality of turns, wherein each turn of the filament is a 360 degree revolution of the filament about the longitudinal axis, and wherein each turn of the filament includes a wave pattern such that adjacent turns of the filament contact one another at a plurality of discrete contact locations. Additionally, a bulk reservoir of molten solder is provided. The wave wound coil is subjected to a quantity of the molten solder, wherein a portion of the quantity of the molten solder is retained at the discrete contact locations while excess amounts of the quantity of molten solder are returned to the bulk reservoir of molten solder. The solder retained at the discrete contact locations is allowed to solidify to fix adjacent turns of the filament together.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
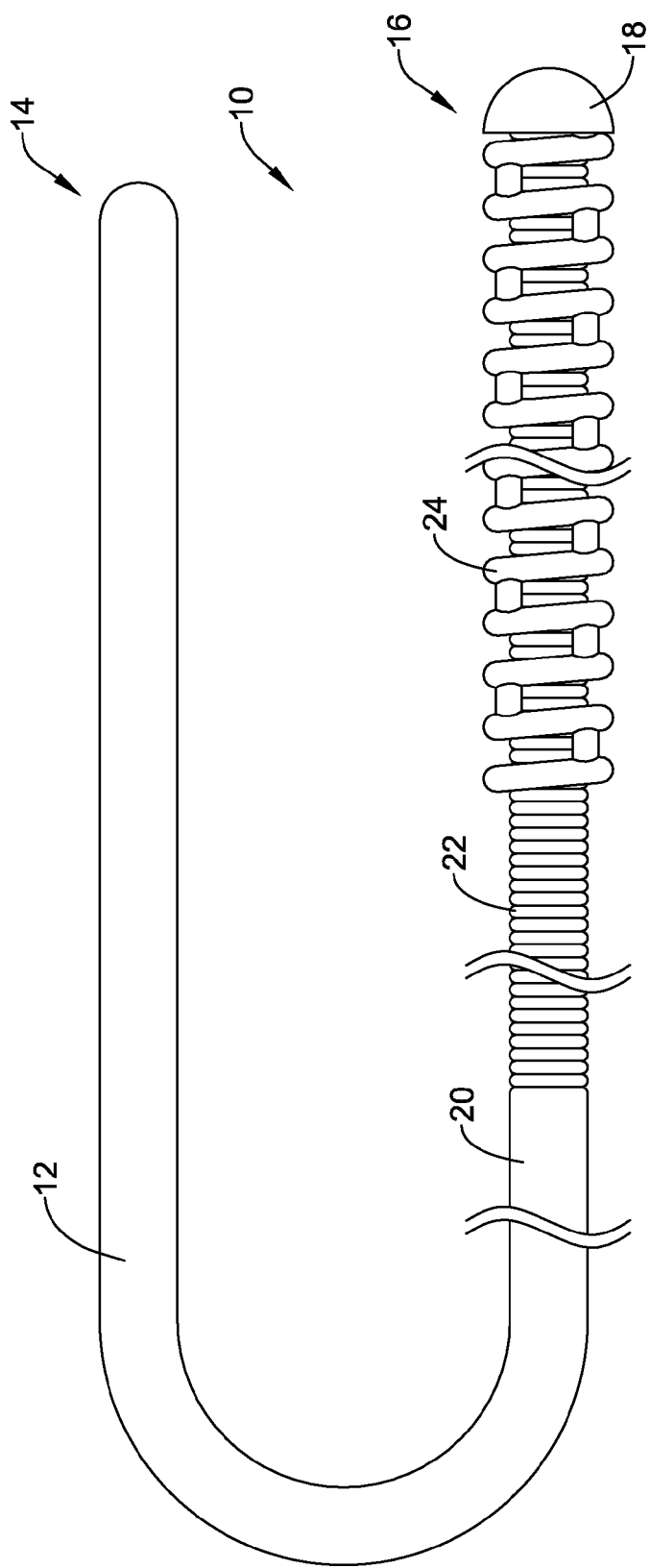
FIG. 1 shows an illustrative guidewire including a coil member.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

It is noted that the figures are included for demonstrative purposes and are schematic in nature. For example, for the sake of clarity, as described herein the welds extending between coil windings and/or the spacing between coil windings are depicted in a schematic nature in various figures, and in application a coil and/or weld may or may not appear dissimilar to that depicted in the figures. For instance, dimensions, shapes and appearance of various components may deviate from those depicted in the figures. Nevertheless, the representation of the coils, welds and other components are intended to provide one of skill in the art with an understanding of the disclosed subject matter. In practice, however one of skill in the art would understand that in some cases the spacing between coils and/or that welds associated with a coil may not necessarily bear a direct resemblance to the coils and/or welds as depicted in the figures, which again, are for demonstrative purposes and are schematic in nature. In addition to the configurations of the welds depicted in FIGS. 1 through 14, FIGS. 15A through 15C illustrate several additional possible configurations of a weld 1304 associated with windings 1302 of a coil as described herein. As shown in FIGS. 15A through 15C, in some embodiments the welds 1304 may resemble a solidified flow of previously molten material fusing two adjacent windings 1302 of a coil together. It is noted that, although not depicted in the figures, still further configurations of a weld securing two adjacent windings of a coil together are also contemplated.

Now referring to the figures, an illustrative guidewire 10 is shown in FIG. 1. The guidewire 10 may include an elongate shaft 12 extending from a proximal end 14 to a distal end 16 and may include a distal tip 18 proximate the distal end 16. The elongate shaft 12 may include a core wire 20, a reinforcing member 22 and/or a modified coil member 24. In some embodiments, the modified coil member 24 may be disposed over the core wire 20 along a portion of the length of the core wire 20. In some embodiments, the reinforcing member 22, shown as a coil, may be disposed between the core wire 20 and the modified coil member 24. The modified coil member 24 may increase the torsional rigidity and torque transmitting properties of the elongate shaft 12 without sacrificing the flexibility characteristics of the shaft 12.

Figure 2:
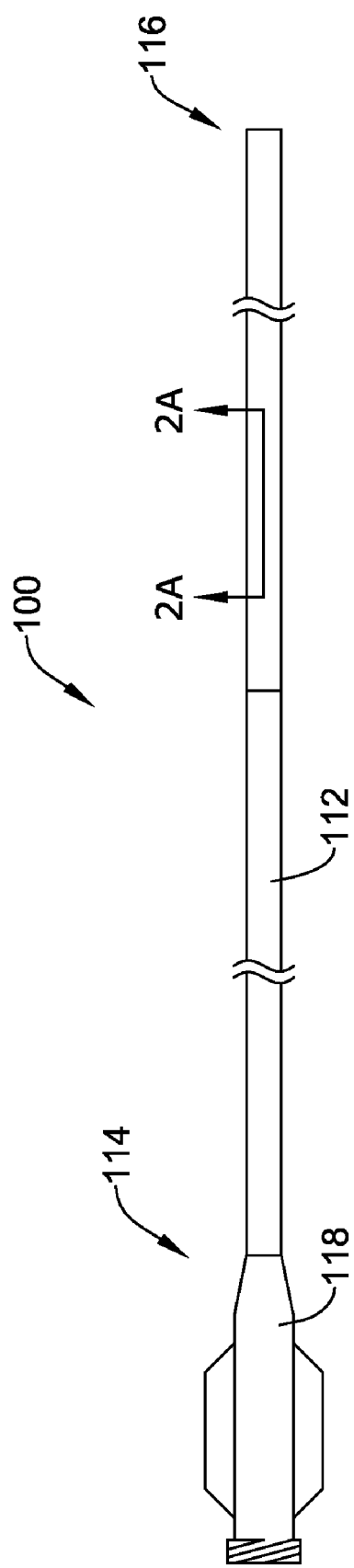
FIG. 2 shows an illustrative catheter including a coil member.

An illustrative catheter 100 is shown in FIG. 2. The catheter 100 may include an elongate shaft 112 extending from a proximal end 114 to a distal end 116 and may include a hub assembly 118 proximate the proximal end 114.

Figure 2A:
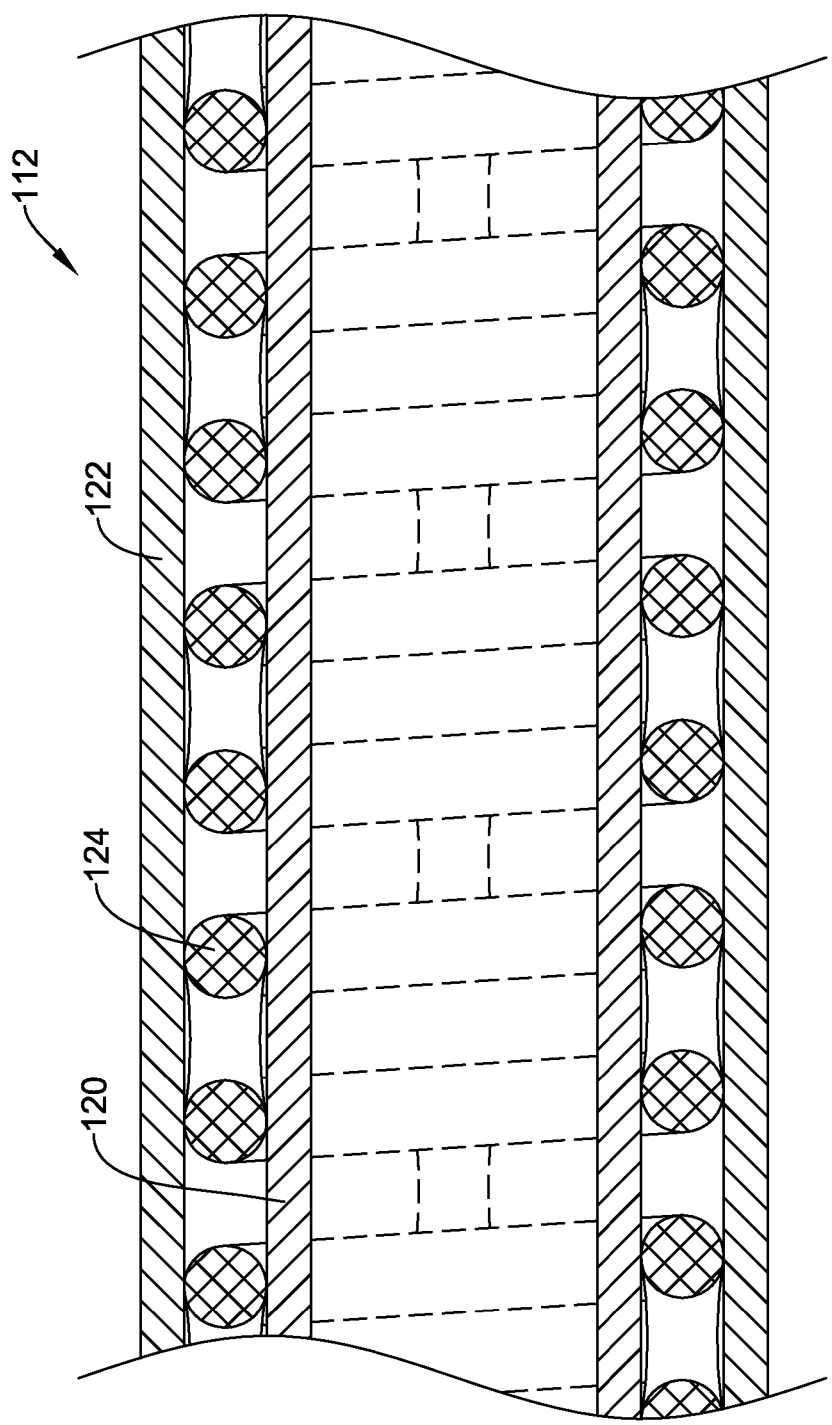
FIG. 2A is a cross-section of the catheter of FIG. 2 taken along line 2A-2A.

As shown in FIG. 2A, the elongate shaft 112 may include an inner liner 120, an outer layer 122 and/or a modified coil member 124. In some embodiments, the elongate shaft 112 may include one or more additional layers or structures as desired. In some embodiments the modified coil member 124 may be disposed between the inner liner 120 and the outer layer 122. The modified coil member 124 may increase the torsional rigidity and torque transmitting properties of the elongate shaft 112 without sacrificing the flexibility characteristics of the shaft 112.

Figure 3:
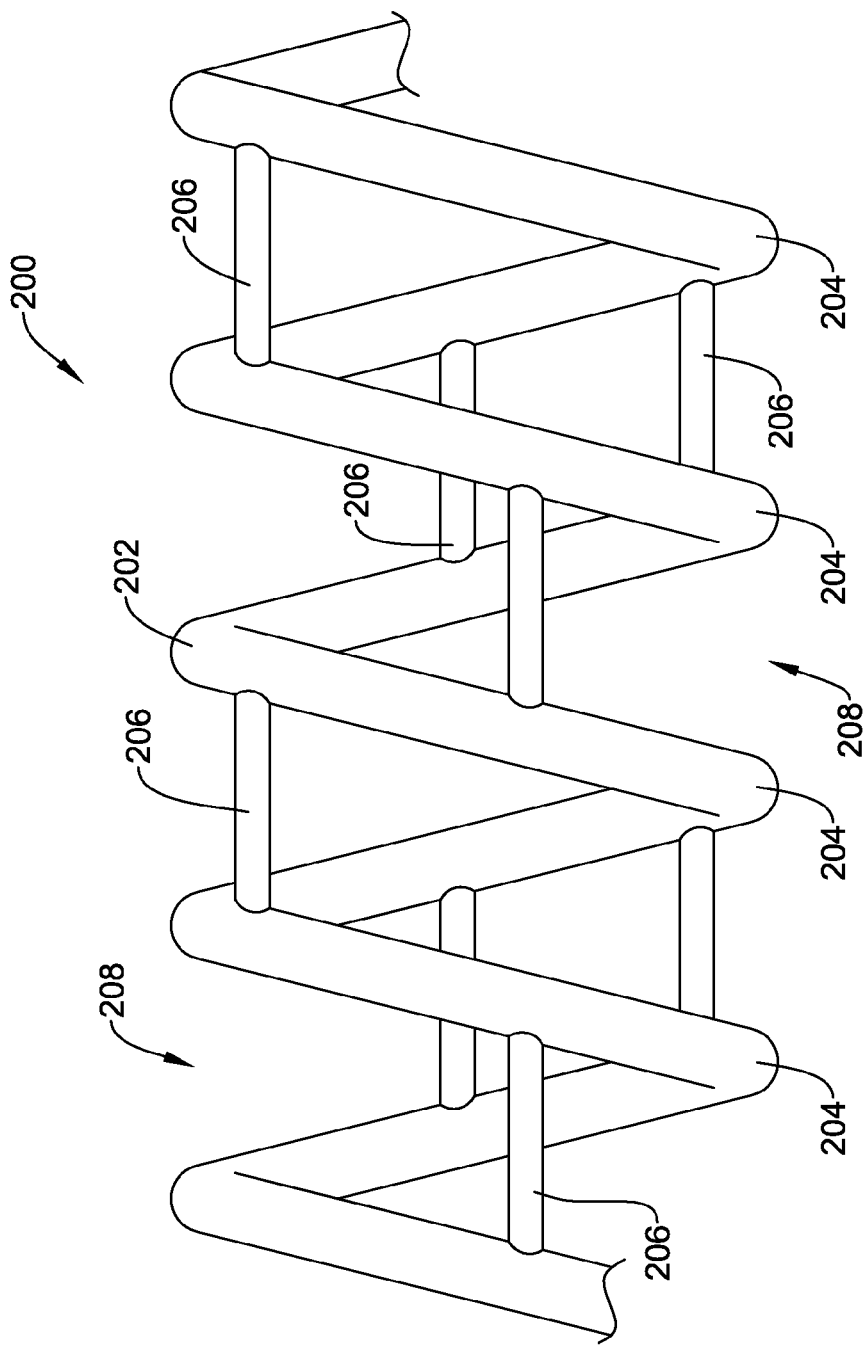
FIG. 3 is a perspective view of an illustrative coil.

An illustrative helical wound coil 200 which may be used in a medical device, such as a guidewire, a catheter, a stent or an embolic coil, for example, is shown in FIG. 3. The coil 200 may be used as the modified coil member 24/124 shown in FIGS. 1 and 2. Thus, specific construction of the coil 200, as well as other coil members and variants described herein, may be incorporated into a medical device, such as the illustrative guidewire 10 of FIG. 1 and/or the illustrative catheter 100 of FIG. 2, as well as other medical devices such as embolic coils and/or stents.

The coil 200 can be formed of a variety of materials including metals, metal alloys, polymers, and the like. Some examples of material for use in the coil 200 include a metal or a metal alloy such as a stainless steel, such as 304V, 304L, and 316L stainless steel; alloys including nickel-titanium alloy such as linear elastic or superelastic (i.e. pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy;

monel 400; inconel 625; or the like; or other suitable material, or combinations or alloys thereof. Some additional examples of suitable material include a polymer material, such as a high performance polymer.

In some embodiments, the coil 200 or portions thereof can be made of, or coated or plated with, or otherwise include a radiopaque material. Radiopaque materials are understood to be materials capable of producing a relatively bright image on a fluoroscopy screen or another imaging technique during a medical procedure. This relatively bright image aids the user of a medical device having the coil 200 in determining its location. Some examples of radiopaque materials can include, but are not limited to, gold, platinum, palladium, tantalum, tungsten alloy, polymer material loaded with a radiopaque filler, and the like, or combinations or alloys thereof.

Additionally, the coil 200, or other portions of a medical device incorporating the coil 200 in its structure, can include materials or structure to impart a degree of MRI compatibility. For example, to enhance compatibility with Magnetic Resonance Imaging (MRI) machines, it may be desirable to make the coil 200, or other portions of the medical device, in a manner that would impart a degree of MRI compatibility. For example, the elongate shaft or core of the medical device, the coil 200, or portions thereof, or other portions of the device, may be made of a material that does not substantially distort the image and create substantial artifacts (artifacts are gaps in the image). Certain ferromagnetic materials, for example, may not be suitable because they may create artifacts in an MRI image. The elongate shaft or core of the medical device, the coil 200, or portions thereof, may also be made from a material that the MRI machine can image. Some materials that exhibit these characteristics include, for example, tungsten, Elgiloy, MP35N, nitinol, and the like, and others, or combinations or alloys thereof.

In some embodiments, the coil 200 can be made of a material that is compatible with a core wire and/or the distal tip of a medical device. The particular material used can be chosen in part based on the desired flexibility requirements or other desired characteristics. In some particular embodiments, the coil 200 can be formed from a superelastic or linear elastic nickel-titanium alloy, for example, linear elastic or superelastic nitinol.

The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL). Within the family of commercially available nitinol alloys, is a category designated "super elastic" (i.e. pseudoelastic) and a category designated "linear elastic". Although these two categories of material are similar in chemistry, they each exhibit distinct and useful mechanical properties. Either, or both superelastic and linear elastic nitinol can be used.

One example of a suitable nickel-titanium alloy that may exhibit linear elastic properties is FHP-NT alloy commercially available from Furukawa Techno Material Co. of Kanagawa, Japan. Some examples of suitable nickel-titanium alloys that may exhibit linear elastic characteristics include those disclosed in U.S. Pat. Nos. 5,238,004 and 6,508,803, which are incorporated herein by reference.

The coil 200, which may be a single filar coil, may be formed of a helically wound filament 202, which in some embodiments may be a round wire or flat ribbon ranging in dimensions to achieve the desired flexibility. In some embodiments in which the filament 202 is a flat ribbon, the flat ribbon may be edge wound. In other words, when a cross-section of the flat ribbon filament 202 is taken, the radial dimension (thickness) of the ribbon filament 202 is greater than the longitudinal dimension (width) of the ribbon filament 202. In other embodiments, the radial dimension (thickness) of the ribbon filament 202 is less than or equal to the longitudinal dimension (width) of the ribbon filament 202. The coil 200 is illustrated as a round wire coil. It can also be appreciated that other cross-sectional shapes or combinations of shapes may be utilized without departing from the spirit of the invention. For example, the cross-sectional shape of wires or filaments used to make the coil 200, as well as other coils described herein, may be oval, rectangular, square, triangle, polygonal, and the like, or any suitable shape. In some embodiments, the coil 200 can be a round ribbon in the range of about 0.001-0.015 inches in diameter, and can have a length in the range of about 0.1 to about 20 inches, however, other dimensions are contemplated.

The coil 200, formed of a wire filament 202, can be wrapped in a helical fashion around a longitudinal axis of the coil 200 by conventional winding techniques to form a plurality of turns or windings 204. The pitch of adjacent turns 204 of the coil 200 may be tightly wrapped so that each turn 204 touches the succeeding turn 204 or the pitch may be set such that the coil 200 is wrapped in an open fashion, leaving a gap 208 between adjacent turns 204 of the coil 200. A single turn or winding 204 of the filament 202 of the coil 200 is a 360 degree revolution of the filament 202 about the longitudinal axis of the coil 200.

As shown in FIG. 3, adjacent coil windings or turns 204 may be connected to each other at discrete locations by a plurality of links. For example, adjacent coil turns 204 may be welded or soldered to one another at discrete locations or welds 206 along the length of the coil 200. Welding or soldering adjacent coil turns 204 at discrete locations or welds 206 may enhance the flexibility and/or torsional properties of the coil 200. For example, welding of adjacent coil turns 204 may increase the torsional rigidity and torque transmitting properties of the coil 200 without sacrificing the flexibility characteristics of the coil 200. The welds 206 between adjacent coil windings or turns 204 may transfer torsional forces along the coil 200 while the coil 200 retains its flexibility. Thus, the coil 200 may possess characteristics similar to those attributed to a slotted tubular member, such as a micromachined hypotube.

In some embodiments, the spacing/arrangement of welds 206, the pitch of turns 204, the cross-sectional dimension (e.g., radial dimension, longitudinal dimension, or diameter) of the filament 202, and/or the inside/outside diameter of the coil 200 may be varied to provide specific torsional properties and/or stiffness/flexibility properties along a desired portion of the coil 200. For instance, a first longitudinal length of the coil 200 may have a first pitch and a second longitudinal length of the coil 200 may have a second pitch dissimilar to the first pitch. Additionally or alternatively, a first length of the filament 202 may have a first cross-sectional dimension (e.g., radial dimension, longitudinal dimension, or diameter) and a second length of the filament 202 may have a second cross-sectional dimension (e.g., radial dimension, longitudinal dimension, or diameter) less than the first cross-sectional dimension. Additionally or alternatively, a first portion of the coil 200 may have a first outer diameter and a second portion of the coil 200 may have a second outer diameter less than the first outer diameter of the coil 200.

In some embodiments, such as that shown in FIG. 3, each turn 204 of the coil 200 may be fixed to an adjacent coil turn 204 at two or more discrete locations or welds 206. In other words, each turn 204 of the coil 200 may be welded or soldered to an adjacent turn 204 at two, three, four, five, six or more discrete locations or welds 206 within a 360 degree revolution of the coil filament 202. Any 360 degree revolution of the filament 202 may be considered a turn 204.

As used herein, "welds" and "welding" include various material joining techniques for uniting two pieces together by heating and allowing a material to reflow and join the two pieces together.

Examples of welding processes that can be suitable in some embodiments include laser welding, resistance welding, TIG welding, micro plasma welding, electron beam welding, sonic welding, solvent welding, and friction or inertia welding. In laser welding a light beam is used to supply the necessary heat. Laser welding can be beneficial in the processes contemplated herein for construction of the coil 200, as the use of a laser light heat source can provide pinpoint accuracy. In some embodiments, laser diode soldering, bulk soldering, wave soldering, brazing, or other soldering technique can be useful. In other embodiments, thermal bonding, adhesive bonding, or other bonding technique may be used.

The bending characteristics of the coil 200 may be controlled, at least in part, by the position of the welds 206. For example, the position of the welds 206 may impart isotropic bending and/or anisotropic bending characteristics on the coil 200. Isotropic bending indicates that the bending stiffness of the coil 200 is uniform in all bending planes parallel to the longitudinal axis of the coil 200, and anisotropic bending indicates that there is preferential bending of the coil 200 in one or more bending planes parallel to the longitudinal axis of the coil 200.

Figure 3A:
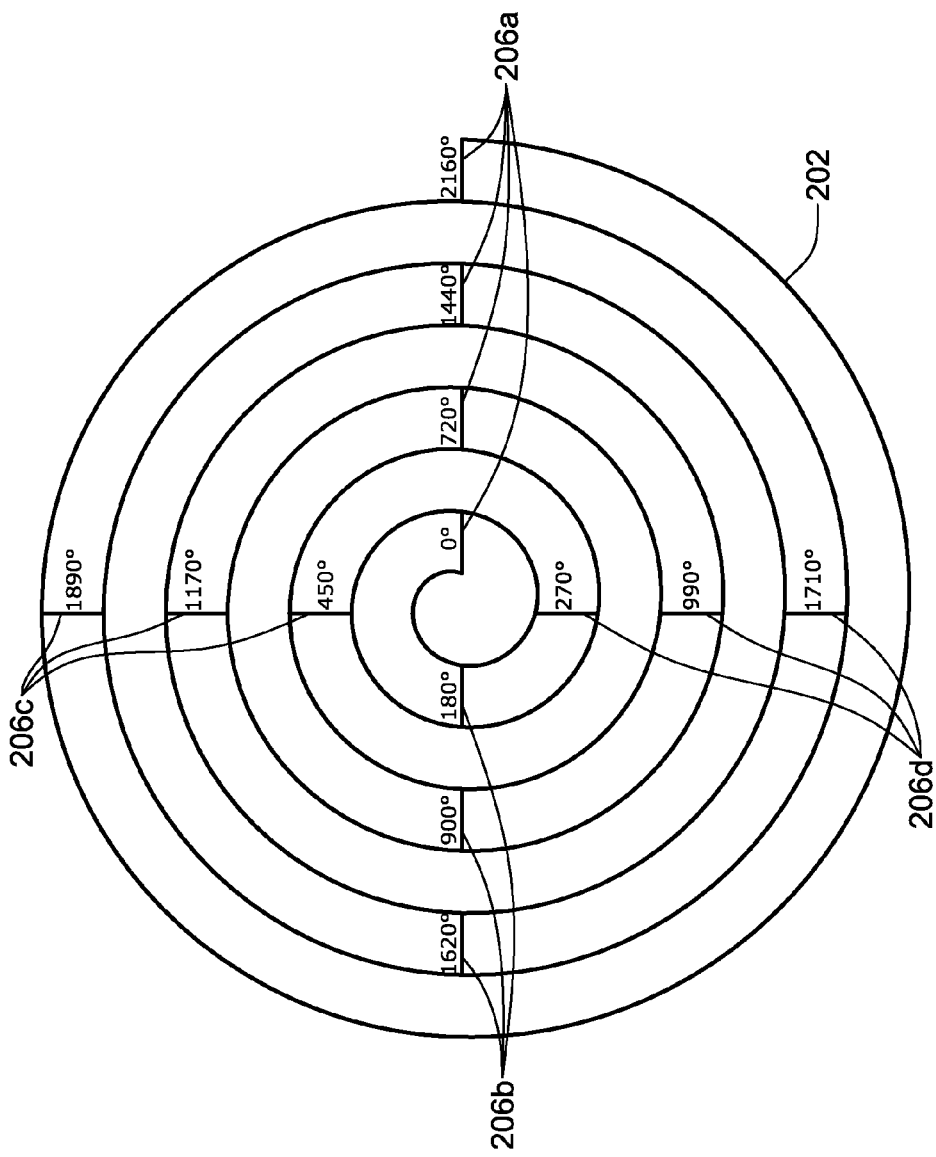
FIG. 3A is illustrative of the pattern of welds of the coil of FIG. 3.

FIG. 3A is an illustrative representation of the location of welds 206 between adjacent turns 204 of the coil 200. In FIG. 3A the filament 202 is shown spiraling outward for illustrative purposes only in order to more easily illustrate the location of welds 206 between adjacent turns 204 of the coil 200. Generally in a medical application, the filament 202 may form a helically wound coil 200 with a generally constant outer diameter. However, in some embodiments the outer diameter of the helically wound coil 200 may vary along at least a portion of the length of the coil 200.

As shown in FIG. 3A, the coil 200 may include welds 206 between windings 204 at 180 degree spacings. In other words, the coil 200 may include a first longitudinal row of welds 206a at a 0 degree radial location and a second longitudinal row of welds 206b at a 180 degree radial location. The coil 200 may also include a third longitudinal row of welds 206c at a 90 degree radial location and a fourth longitudinal row of welds 206d at a 270 degree radial location. At each radial location (e.g., 0, 90, 180 and 270 degrees) the welds 206 may fix together a first turn of the filament 202 with a second turn of the filament 202, may fix together a third turn of the filament 202 with a fourth turn of the filament 202, may fix together a fifth turn of the filament 202 with a sixth turn of the filament 202, etc. Furthermore, no weld may be located at each radial location (e.g., 0, 90, 180 and 270 degrees) between the second turn of the filament 202 and the third turn of the filament 202, between the fourth turn of the filament 202 and the fifth turn of the filament 202, etc. In other words, at a given radial location (e.g., 0, 90, 180 and 270 degrees) welds 206 may be present at every other gap 208 between successive turns of the coil 200. In other embodiments, at a given radial location (e.g., 0, 90, 180 and 270 degrees) welds 206 may be present at every third gap 208 between successive turns of the coil 200, or at every fourth gap 208 between successive turns of the coil 200, for example, or other spacings as desired.

Figure 4:
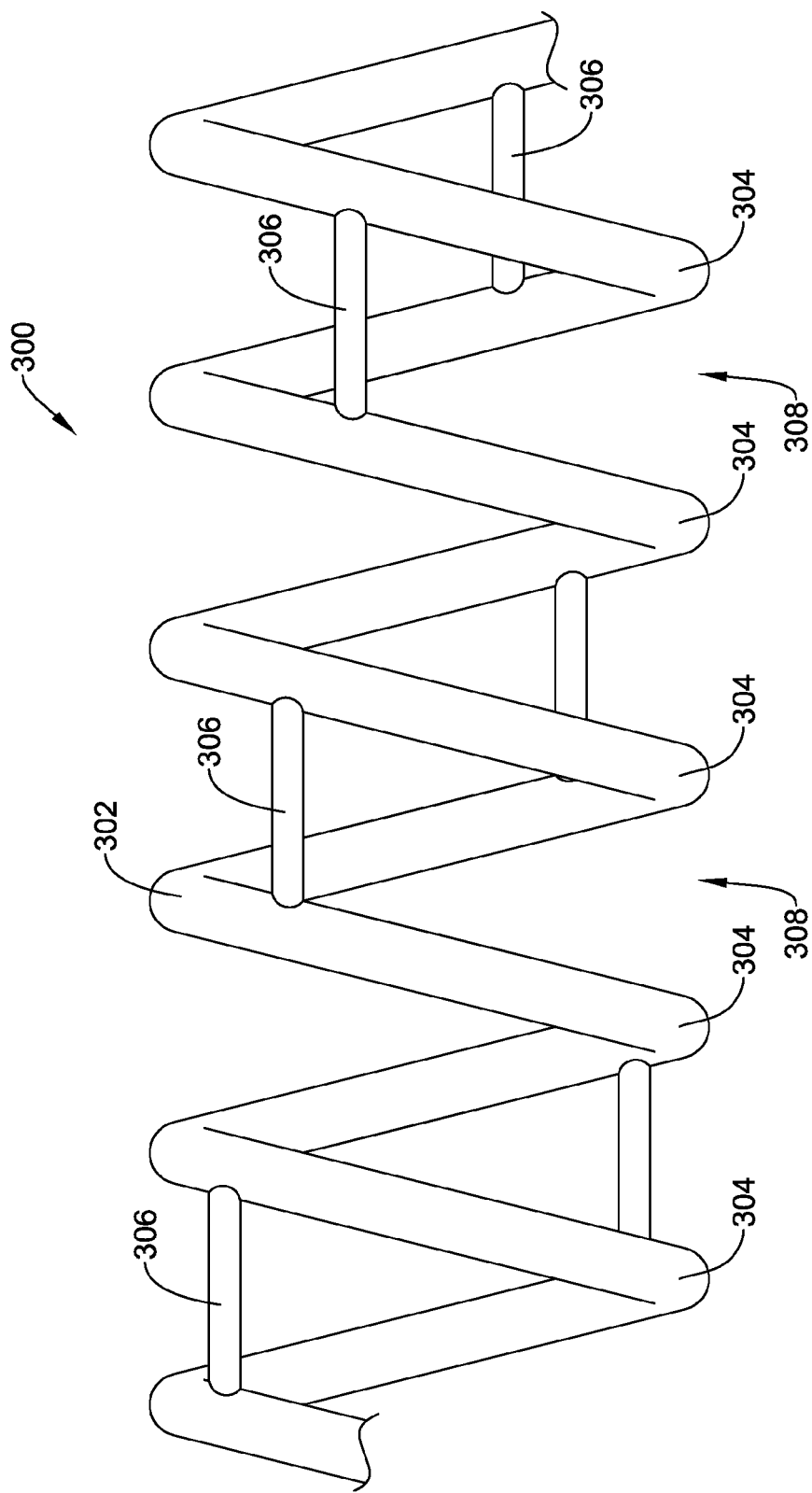
FIG. 4 is a perspective view of another illustrative coil.

An alternate embodiment of a coil 300, similar to the coil 200, is shown in FIG. 4. In the interest of brevity, similarities in construction and operation of the coil 300 with the coil 200 will not be reiterated.

The coil 300, which may be a single filar coil, may be formed of a helically wound filament 302, which in some embodiments may be a round wire or flat ribbon ranging in dimensions to achieve the desired flexibility. In some embodiments in which the filament 302 is a flat ribbon, the flat ribbon may be edge wound. In other words, when a cross-section of the flat ribbon filament 302 is taken, the radial dimension (thickness) of the ribbon filament 302 is greater than the longitudinal dimension (width) of the ribbon filament 302. In other embodiments, the radial dimension (thickness) of the ribbon filament 302 is less than or equal to the longitudinal dimension (width) of the ribbon filament 302. The coil 300 is illustrated as a round wire coil. The coil 300, formed of a wire filament 302, can be wrapped in a helical fashion around a longitudinal axis of the coil 300 by conventional winding techniques to form a plurality of turns or windings 304. The pitch of adjacent turns 304 of the coil 300 may be tightly wrapped so that each turn 304 touches the succeeding turn 304 or the pitch may be set such that the coil 300 is wrapped in an open fashion, leaving a gap 308 between adjacent turns 304 of the coil 300. A single turn or winding 304 of the filament 302 of the coil 300 is a 360 degree revolution of the filament 302 about the longitudinal axis of the coil 300.

As shown in FIG. 4, adjacent coil windings or turns 304 may be connected to each other at discrete locations by a plurality of links. For example, adjacent coil turns 304 may be welded or soldered to one another at discrete locations or welds 306 along the length of the coil 300. Welding or soldering adjacent coil turns 304 at discrete locations or welds 306 may enhance the flexibility and/or torsional properties of the coil 300. For example, welding of adjacent coil turns 304 may increase the torsional rigidity and torque transmitting properties of the coil 300 without sacrificing the flexibility characteristics of the coil 300. The welds 306 between adjacent coil windings or turns 304 may transfer torsional forces along the coil 300 while the coil 300 retains its flexibility. Thus, the coil 300 may possess characteristics similar to those attributed to a slotted tubular member, such as a micromachined hypotube.

In some embodiments, such as that shown in FIG. 4, each turn 304 of the coil 300 may be fixed to an adjacent coil turn 304 at two or more discrete locations or welds 306. In other words, each turn 304 of the coil 300 may be welded or soldered to an adjacent turn 304 at two, three, four, five, six or more discrete locations or welds 306 within a 360 degree revolution of the coil filament 302. Any 360 degree revolution of the filament 302 may be considered a turn 304.

The bending characteristics of the coil 300 may be controlled, at least in part, by the position of the welds 306. For example, the position of the welds 306 may impart isotropic bending and/or anisotropic bending characteristics on the coil 300. Isotropic bending indicates that the bending stiffness of the coil 300 is uniform in all bending planes parallel to the longitudinal axis of the coil 300, and anisotropic bending indicates that there is preferential bending of the coil 300 in one or more bending planes parallel to the longitudinal axis of the coil 300.

Figure 4A:
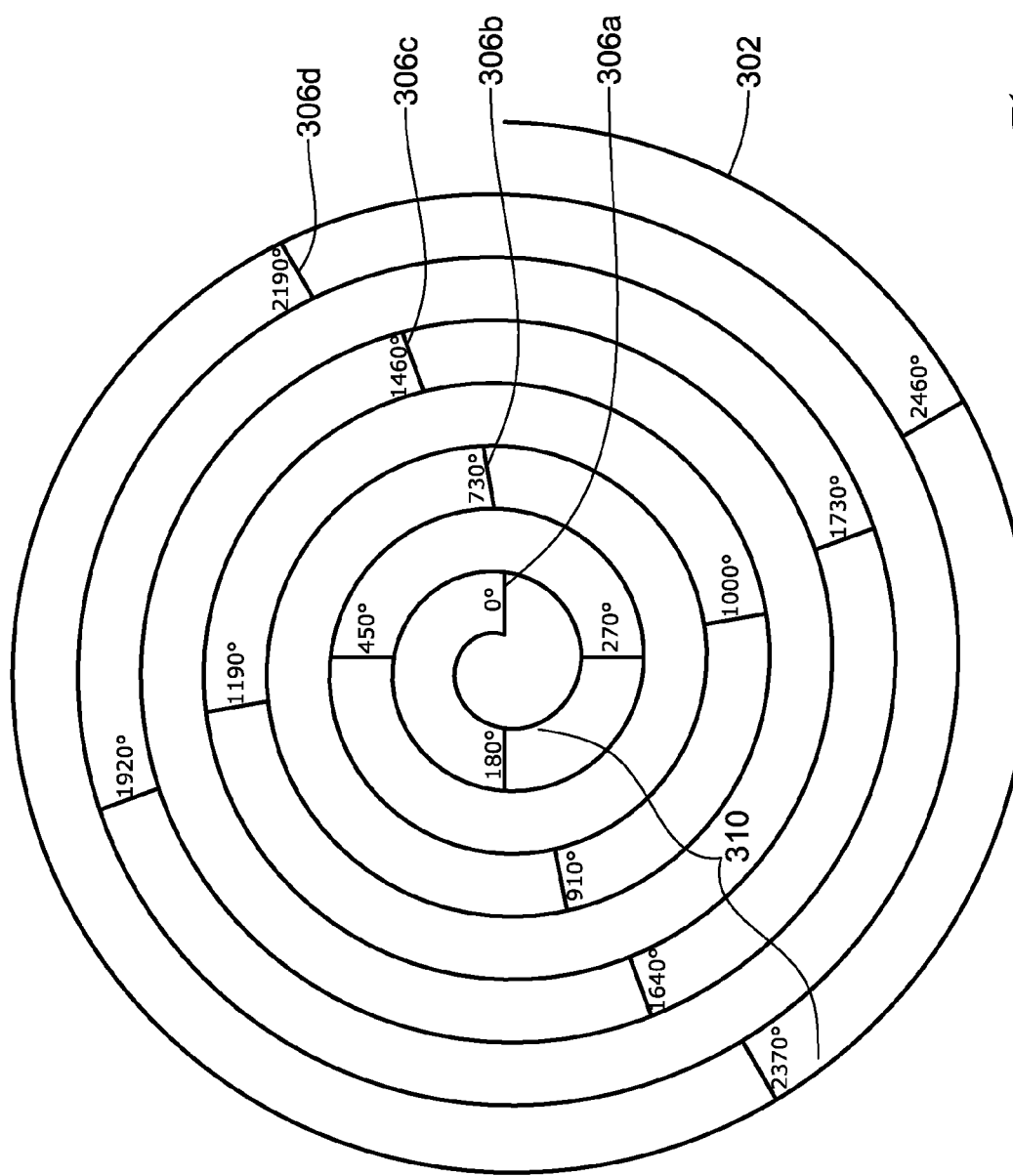
FIG. 4A is illustrative of the pattern of welds of the coil of FIG. 4.

FIG. 4A is an illustrative representation of the location of welds 306 between adjacent turns 304 of the coil 300. In FIG. 4A the filament 302 is shown spiraling outward for illustrative purposes only in order to more easily illustrate the location of welds 306 between adjacent turns 304 of the coil 300. Generally in a medical application, the filament 302 may form a helically wound coil 300 with a generally constant outer diameter.

As shown in FIG. 4A, the coil 300 may include welds 306 between windings 304 at progressively varying radial locations, providing the coil 300 with isotropic bending characteristics. In other words, the coil 300 may include a first weld 306a at a 0 degree radial location and a second weld 306b radially offset from the first weld 306a by a few degrees. For example, in some embodiments the second weld 306b may be radially offset from the first weld 306a by about 2, 5, 10, or 20 degrees. The first weld 306a may fix a first turn of the coil 300 with a second turn, and the second weld 306b may fix a third turn of the coil 300 with a fourth turn. A third weld 306c may be radially offset from the second weld 306b by a few degrees, for example, by about 2, 5, 10 or 20 degrees, and thus offset from the first weld 306a, by the additional amount. The third weld 306c may fix a fifth turn of the coil 300 with a sixth turn. A fourth weld 306d may be radially offset from the third weld 306c by a few degrees, for example, about 2, 5, 10 or 20 degrees, and thus offset from the first and second welds 306a, 306b by the additional amount. The fourth weld 306d may fix a seventh turn of the coil 300 with an eighth turn. In some embodiments, the first and second welds 306a, 306b may be positioned about 720+/−2 degrees, 720+/−5 degrees, 720+/−10 degrees, or 720+/−20 degrees from one another, for example. In some embodiments, the second and third welds 306b, 306c may be positioned about 720+/−2 degrees, 720+/−5 degrees, 720+/−10 degrees, or 720+/−20 degrees from one another, for example. In some embodiments, the third and fourth welds 306c, 306d may be positioned about 720+/−2 degrees, 720+/−5 degrees, 720+/−10 degrees, or 720+/−20 degrees from one another, for example.

Thus, the welds between a third turn and a fourth turn of the filament may be phase shifted from the welds between a first turn and a second turn, and the welds between a fifth turn and a sixth turn of the filament may be phase shifted from the welds between the third turn and the fourth turn and may be phased shifted from the welds between the first turn and the second turn. For instance, the first turn may be welded to the second turn at about a 0 degree location and at about a 180 degree location. The third turn may be welded to the fourth turn at about a 2, 5, 10 or 20 degree location and at about a 182, 185, 190 or 200 degree location, respectively. The fifth turn may be welded to the sixth turn at about a 4, 10, 20 or 40 degree location and at about a 184, 190, 200, or 200 degree location, respectively.

Thus, as shown in FIG. 4A, the coil 300 may include a helical row of welds 310 helically revolving around the coil 300. The coil 300 may include additional helical rows of welds 310 helically revolving around the coil 300 at additional radial locations. For example, a second, third and/or fourth helically rotating row of welds 310 may be offset from the first helical row of welds 310 at a 90, 180, and/or 270 degree radial interval in some embodiments. Thus, each helical row of welds 310 may fix together a first turn of the filament 302 with a second turn of the filament 302, may fix together a third turn of the filament 302 with a fourth turn of the filament 302, may fix together a fifth turn of the filament 302 with a sixth turn of the filament 302, etc. In other words, in each helical row of welds 310, a weld 306 may be present at every other gap 308 between successive turns of the coil 300. In other embodiments, a weld 306 each helical row of welds 310 may be present at every third gap 308 between successive turns of the coil 300, or every fourth gap 308 between successive turns of the coil 300, for example, or other spacing as desired.

Figure 5:
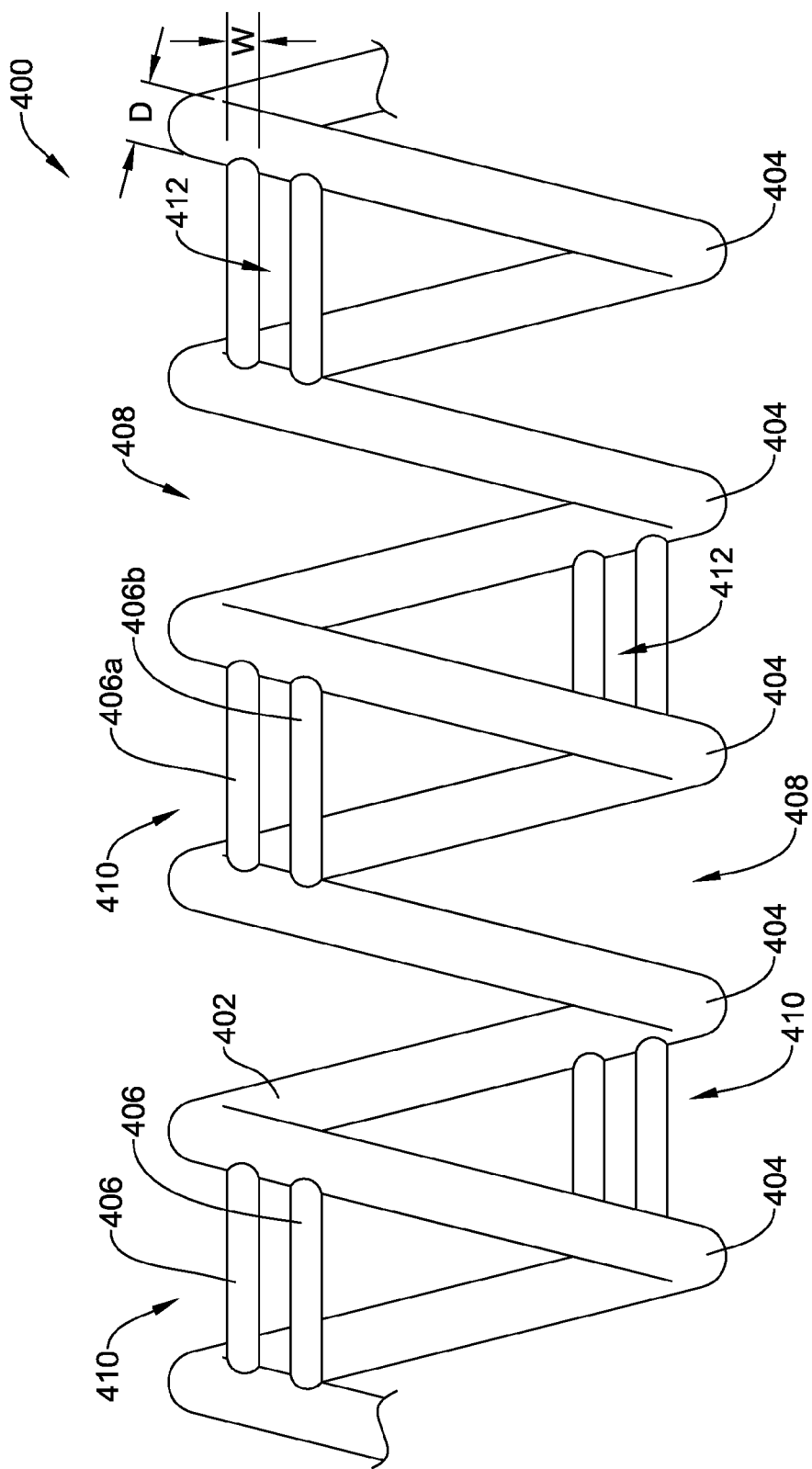
FIG. 5 is a perspective view of yet another illustrative coil.

An alternate embodiment of a coil 400, similar to the coils 200, 300 is shown in FIG. 5. In the interest of brevity, similarities in construction and operation of the coil 400 with the coils 200, 300 will not be reiterated.

The coil 400, which may be a single filar coil, may be formed of a helically wound filament 402, which in some embodiments may be a round wire or flat ribbon ranging in dimensions to achieve the desired flexibility. In some embodiments in which the filament 402 is a flat ribbon, the flat ribbon may be edge wound. In other words, when a cross-section of the flat ribbon filament 402 is taken, the radial dimension (thickness) of the ribbon filament 402 is greater than the longitudinal dimension (width) of the ribbon filament 402. In other embodiments, the radial dimension (thickness) of the ribbon filament 402 is less than or equal to the longitudinal dimension (width) of the ribbon filament 402. The coil 400 is illustrated as a round wire coil. The coil 400, formed of a filament 402, can be wrapped in a helical fashion around a longitudinal axis of the coil 400 by conventional winding techniques to form a plurality of turns or windings 404. The pitch of adjacent turns 404 of the coil 400 may be tightly wrapped so that each turn 404 touches the succeeding turn 404 or the pitch may be set such that the coil 400 is wrapped in an open fashion, leaving a gap 408 between adjacent turns 404 of the coil 400. A single turn or winding 404 of the filament 402 of the coil 400 is a 360 degree revolution of the filament 402 about the longitudinal axis of the coil 400.

As shown in FIG. 5, adjacent coil windings or turns 404 may be connected to each other at discrete locations. For example, adjacent coil turns 404 may be welded or soldered to one another at discrete locations or welds 406 along the length of the coil 400. Welding or soldering adjacent coil turns 404 at discrete locations or welds 406 may enhance the flexibility and/or torsional properties of the coil 400. For example, welding of adjacent coil turns 404 may increase the torsional rigidity and torque transmitting properties of the coil 400 without sacrificing the flexibility characteristics of the coil 400. The welds 406 between adjacent coil windings or turns 404 may transfer torsional forces along the coil 400 while the coil 400 retains its flexibility. Thus, the coil 400 may possess characteristics similar to those attributed to a slotted tubular member, such as a micromachined hypotube.

In some embodiments, such as that shown in FIG. 5, each turn 404 of the coil 400 may be fixed to an adjacent coil turn 404 at two or more discrete locations or welds 406. In other words, each turn 404 of the coil 400 may be welded or soldered to an adjacent turn 404 at two, three, four, five, six or more discrete locations or welds 406 within a 360 degree revolution of the coil filament 402. Any 360 degree revolution of the filament 402 may be considered a turn 404.

The bending characteristics of the coil 400 may be controlled, at least in part, by the position of the welds 406. For example, the position of the welds 406 may impart isotropic bending and/or anisotropic bending characteristics on the coil 400. Isotropic bending indicates that the bending stiffness of the coil 400 is uniform in all bending planes parallel to the longitudinal axis of the coil 400, and anisotropic bending indicates that there is preferential bending of the coil 400 in one or more bending planes parallel to the longitudinal axis of the coil 400.

As shown in FIG. 5, each turn 404 of the coil 400 may be fixed to an adjacent coil turn 404 by a weld grouping 410 including a plurality of welds 406. Each weld grouping 410 may include two, three, four or more welds 406 positioned together to form a unit. In some embodiments, the individual welds 406 of a weld grouping 410 may have a width, w, equal to about one, two, three, or four times the cross-sectional dimension, d, of the filament 402 of the coil 400. Individual welds 406 of a weld grouping 410 may be located in close proximity to one another, and may collectively span the gap 408 between adjacent turns 404 of the coil 400. In some embodiments individual welds 406 of a weld grouping 410 may abut one another, leaving no space between the individual welds 406 of a weld grouping 410. In other embodiments, such as shown in FIG. 5, a space 412 may be present between individual welds 406 of a weld grouping 410. For example, a first weld 406a may be spaced from a second weld 406b of a weld grouping 410 by a distance approximately equal to one, two, three, or four times the cross-sectional dimension of the filament 402 of the coil 400. In some embodiments, the space 412 may be less than four times, less than three times, less than two times, or less than one times the cross-sectional dimension of the filament 402 of the coil 400. The close proximity of the individual welds 406 of a weld grouping 410 acts to approximate a single larger weld bridging adjacent turns 404 of the coil 400.

Figure 5A:
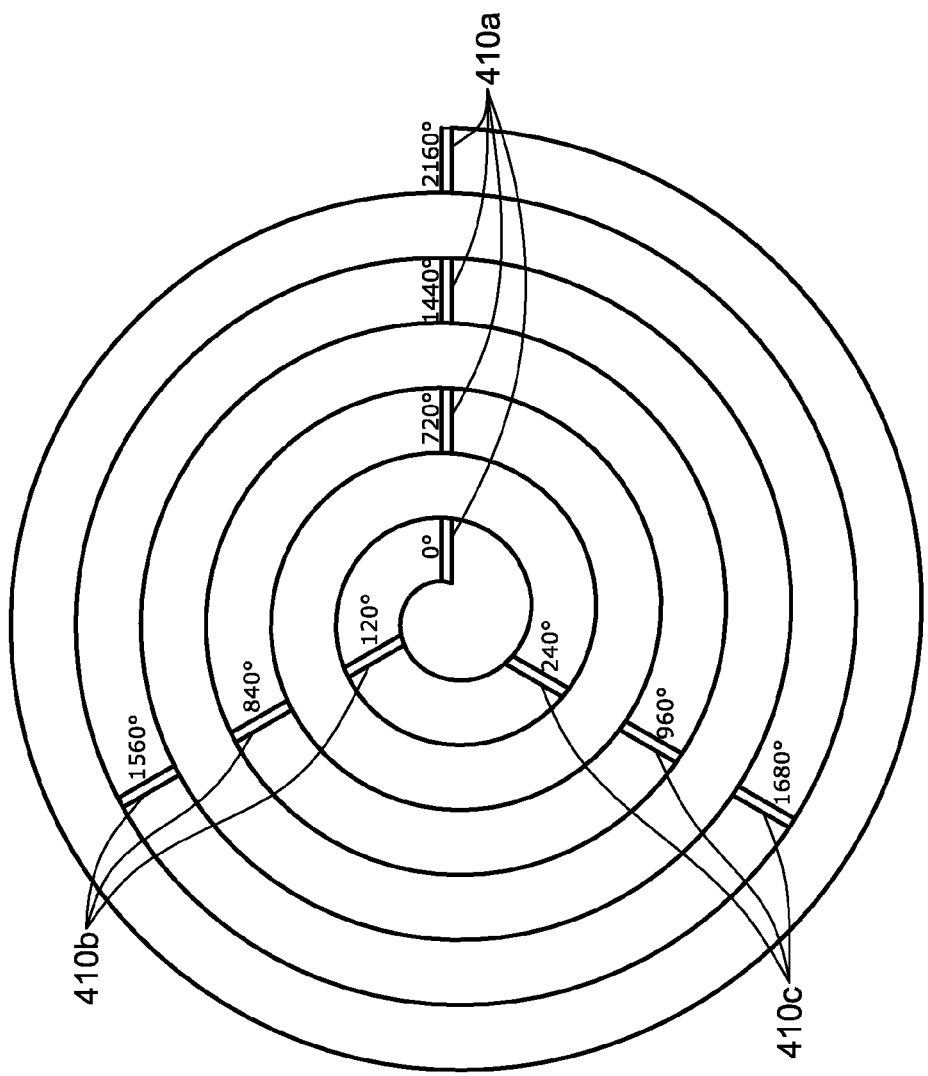
FIG. 5A is illustrative of the pattern of welds of the coil of FIG. 5.

FIG. 5A is an illustrative representation of the location of welds 406 of the weld groupings 410 between adjacent turns 404 of the coil 400. In FIG. 5A the filament 402 is shown spiraling outward for illustrative purposes only in order to more easily illustrate the location of welds 406 between adjacent turns 404 of the coil 400. Generally in a medical application, the filament 402 may form a helically wound coil 400 with a generally constant outer diameter.

As shown in FIG. 5A, the coil 400 may include weld groupings 410 of a plurality of welds 406 between windings 404 at 120 degree spacings. In other words, the coil 400 may include a first longitudinal row of weld groupings 410a at a 0 degree radial location and a second longitudinal row of weld groupings 410b at a 120 degree radial location. The coil 400 may also include a third longitudinal row of weld groupings 410c at a 240 degree radial location. At each radial location (e.g., 0, 120, and 240 degrees) the weld groupings 410 may fix together a first turn of the filament 402 with a second turn of the filament 402, may fix together a third turn of the filament 402 with a fourth turn of the filament 402, may fix together a fifth turn of the filament 402 with a sixth turn of the filament 402, etc. Furthermore, no weld may be located at each radial location (e.g., 0, 120, and 240 degrees) between the second turn of the filament 402 and the third turn of the filament 402, between the fourth turn of the filament 402 and the fifth turn of the filament 402, etc. In other words, at a given radial location (e.g., 0, 120, and 240 degrees) weld groupings 410 may be present at every other gap 408 between successive turns of the coil 400. In other embodiments, at a given radial location (e.g., 0, 120, and 240 degrees) weld groupings 410 may be present at every third gap 408 between successive turns of the coil 400, or at every fourth gap 408 between successive turns of the coil 400, for example, or other spacings as desired.

Figure 6A:
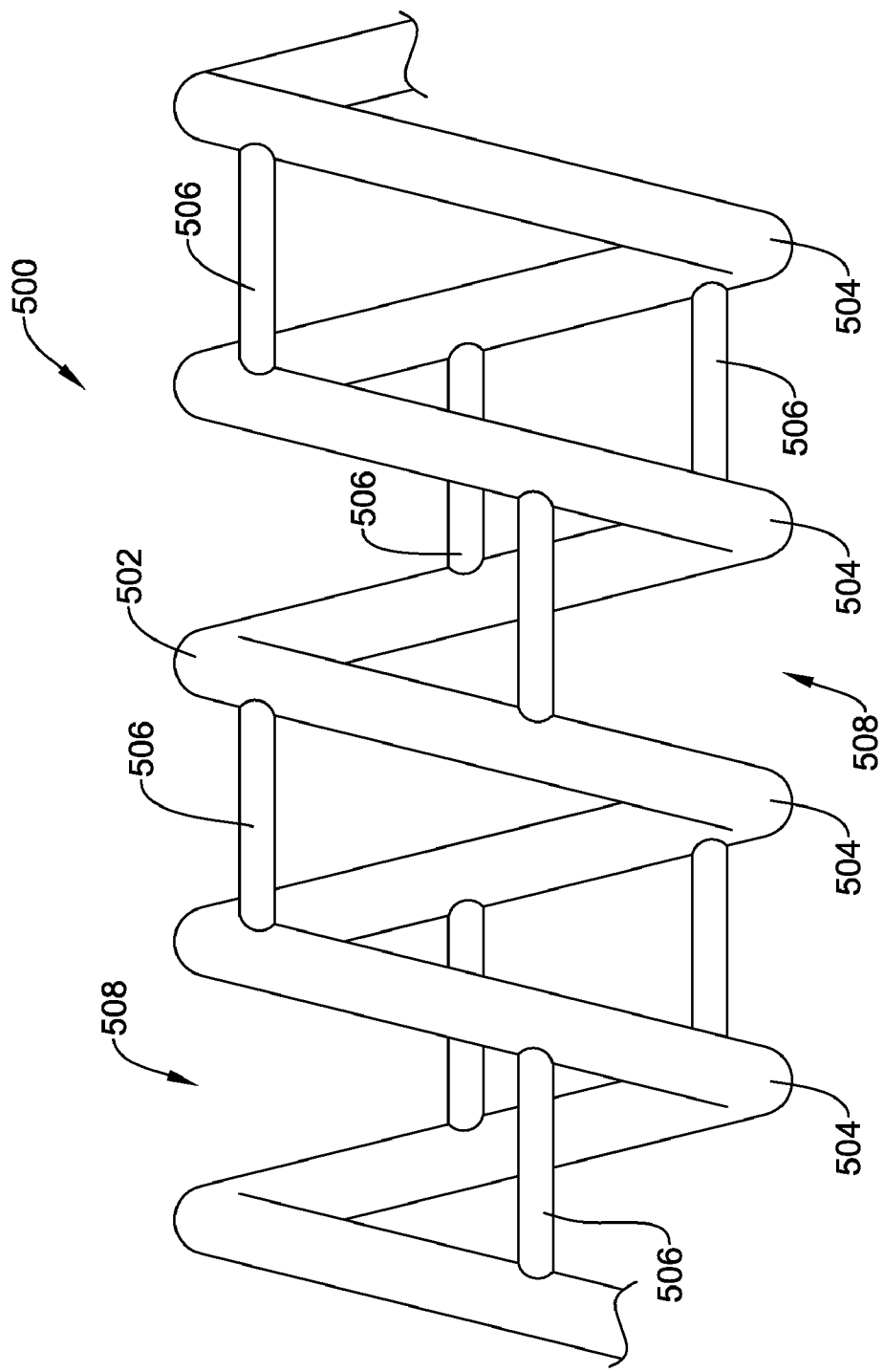
FIGS. 6A-6B illustrate another exemplary coil and a method of forming the coil.
Figure 6B:
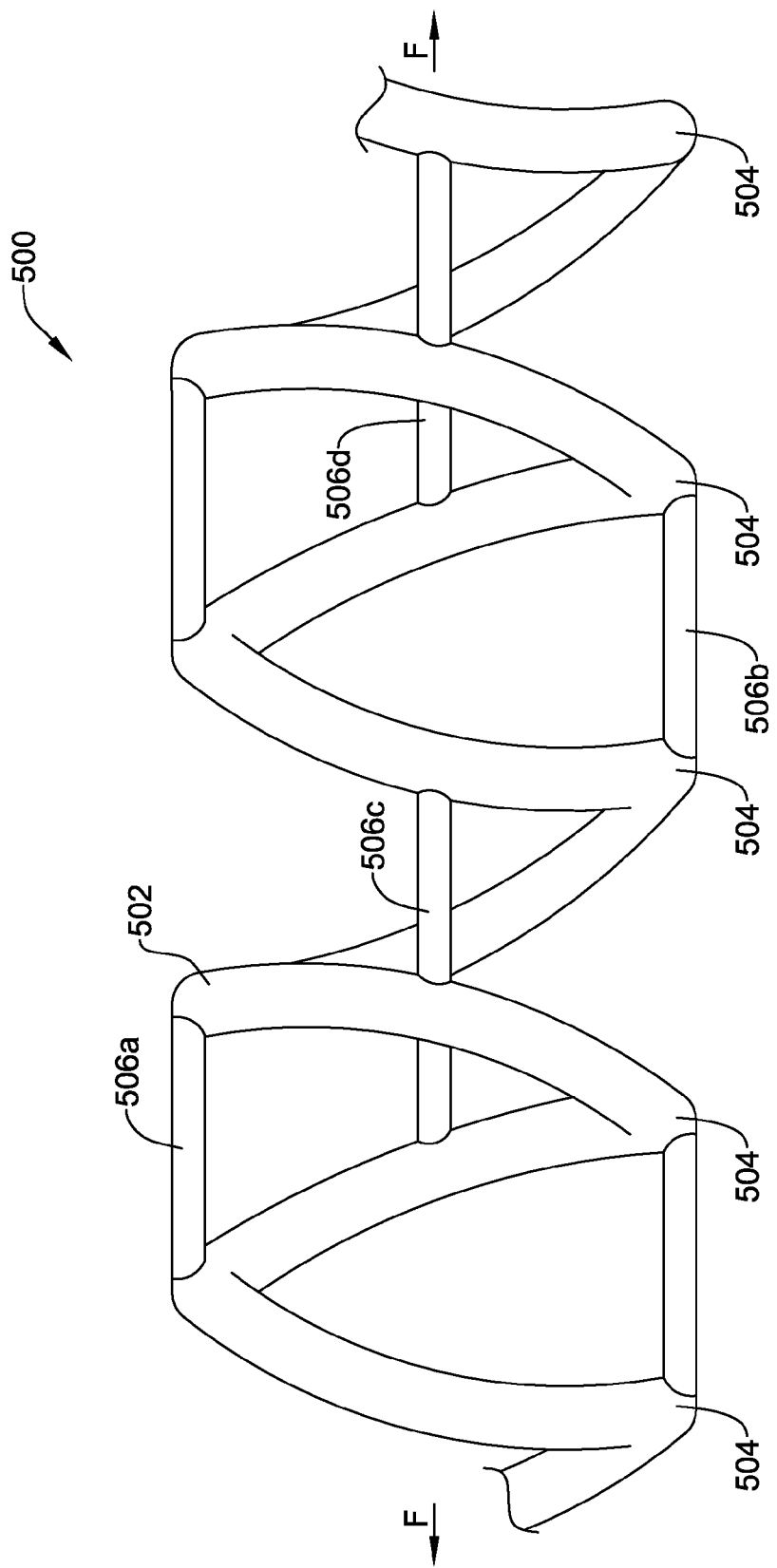

Another coil 500 and method of forming the coil 500 is shown in FIGS. 6A and 6B. Initially, as shown in FIG. 6A, the coil 500 may be provided as a helically wound coil in which adjacent turns 504 of the filament 502 forming the coil 500 are in a parallel arrangement. In other words, initially adjacent turns 504 of the filament 502 forming the coil 500 are parallel to one another. A plurality of welds 506 may be formed between adjacent turns 504 of the coil 500 at select discrete locations along the length of the coil 500.

In the embodiment shown in FIG. 6A, each turn 504 of the coil 500 may be fixed to an adjacent coil turn 504 at two discrete locations or welds 506. In other words, each turn 504 of the coil 500 may be welded to an adjacent turn 504 at two discrete locations or welds 506 within a 360 degree revolution of the coil filament 502. Any 360 degree revolution of the filament 502 may be considered a turn 504. In other embodiments, each turn 504 of the coil 500 may be fixed to an adjacent coil turn 504 at any number of discrete locations or welds 506.

As shown in FIG. 6A, the coil 500 may include welds 506 between windings 504 at 180 degree spacings. In other words, the coil 500 may include a first longitudinal row of welds 506a at a 0 degree radial location and a second longitudinal row of welds 506b at a 180 degree radial location. The coil 500 may also include a third longitudinal row of welds 506c at a 90 degree radial location and a fourth longitudinal row of welds 506d at a 270 degree radial location. At each radial location (e.g., 0, 90, 180 and 270 degrees) the welds 506 may fix together a first turn of the filament 502 with a second turn of the filament 502, may fix together a third turn of the filament 502 with a fourth turn of the filament 502, may fix together a fifth turn of the filament 502 with a sixth turn of the filament 502, etc. Furthermore, no weld may be located at each radial location (e.g., 0, 90, 180 and 270 degrees) between the second turn of the filament 502 and the third turn of the filament 502, between the fourth turn of the filament 502 and the fifth turn of the filament 502, etc. In other words, at a given radial location (e.g., 0, 90, 180 and 270 degrees) welds 506 may be present at every other gap 508 between successive turns of the coil 500. In other embodiments, at a given radial location (e.g., 0, 90, 180 and 270 degrees) welds 506 may be present at every third gap 508 between successive turns of the coil 500, or at every fourth gap 508 between successive turns of the coil 500, for example, or other spacings as desired.

After fixing select coil turns 504 together with welds 506, the geometry of the coil 500 may be further modified by stretching the coil 500 longitudinally. As shown in FIG. 6B, a longitudinal force F may be applied to the coil 500 subsequent to connecting adjacent turns or windings 504 with welds 506. As a result of longitudinally stretching the coil 500, it can be seen that adjacent coil turns or windings 504 are no longer parallel to one another. This structure may incorporate different, desired physical properties into the modified coil 500 throughout this elongated region. Properties such as compressive strength, bending stiffness and torsional stiffness may all be varied as a result of a stretching operation such as this. It is noted that the entire length of the coil 500 may be modified by stretching the coil 500, or a select portion of the length, less than the entire length, of the coil 500 may be modified by stretching the coil 500 subsequent to welding adjacent windings or turns 504.

Figure 7:
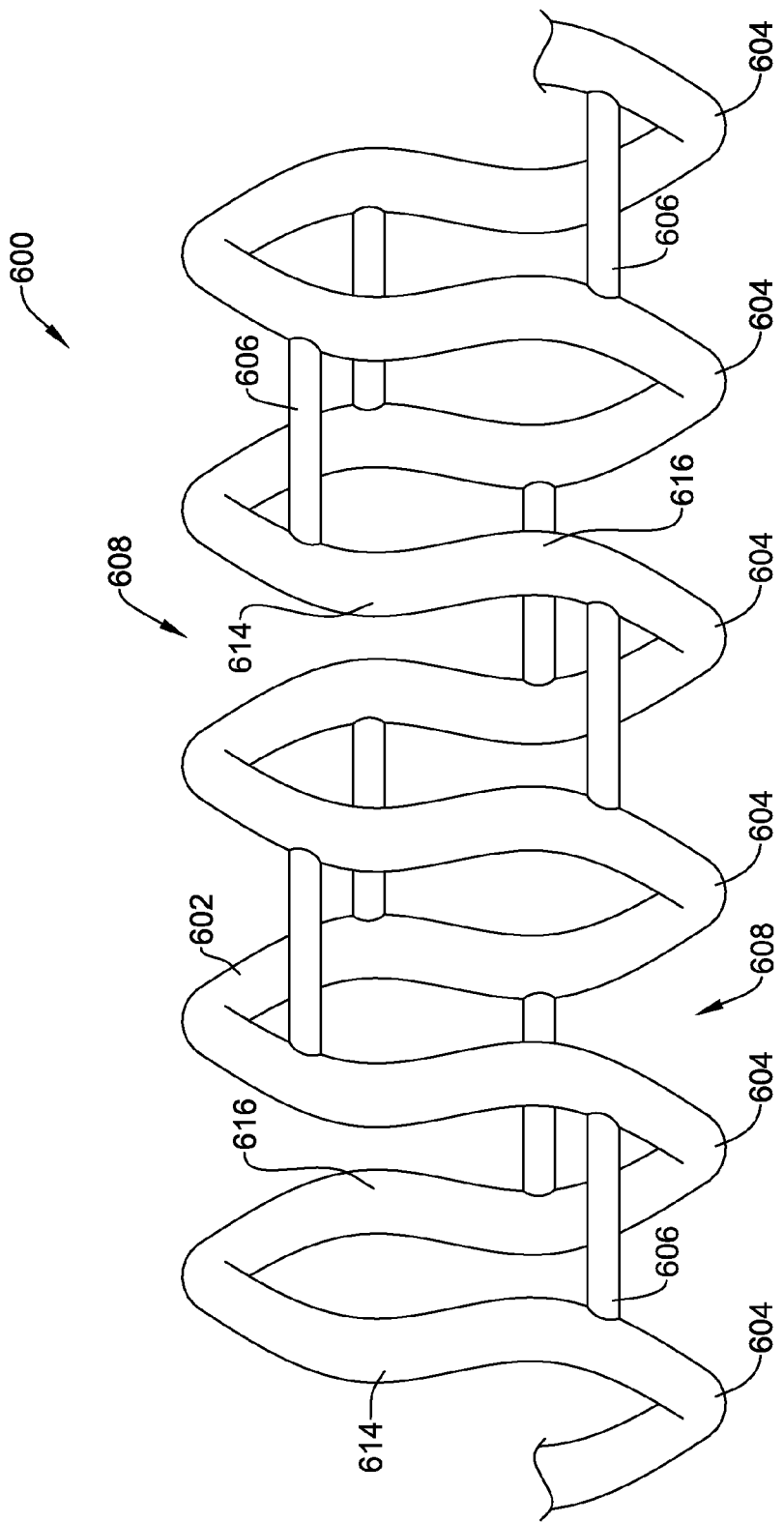
FIG. 7 illustrates an exemplary nested wave wound coil.

A nested wave wound coil 600 having a longitudinal axis is shown in FIG. 7. The nested wave wound coil 600 may include a filament 602 helically wound around the longitudinal axis of the coil 600 to form a plurality of turns or windings 604. As shown in FIG. 7, the filament 602 may be a round wire filament. However, in other embodiments the filament 602 may has a different cross-sectional geometry. For example, in some embodiments the filament 602 may be a flat ribbon filament which may or may not be edge-wound. The pitch of adjacent turns 604 of the coil 600 may be tightly wrapped so that each turn 604 touches the succeeding turn 604 or the pitch may be set such that the coil 600 is wrapped in an open fashion, leaving a gap 608 between adjacent turns 604 of the coil 600. A single turn or winding 604 of the filament 602 of the coil 600 is a 360 degree revolution of the filament 602 about the longitudinal axis of the coil 600.

Each turn 604 may include a wave pattern of high periods and low periods. The orthogonal distance between the peak deviation of the high periods and/or low periods and the imaginary base line of the wave is considered the amplitude of the wave. Each turn 604 may include two or more crests 614 and two or more troughs 616 of a wave pattern extending around the circumference of the coil 600. In an exemplary embodiment, each turn 604 may include two crests 614 and two troughs 616. However, in other embodiments, each turn 604 may include any desired number of crests 614 and troughs 616. A wavelength is considered one complete cycle of the wave pattern. A standard nested wave wound coil would have an even integer multiple of ½ wavelengths per turn 604 of the filament 602. In other words, each winding or turn 604 of the filament 602 would have an integer number of wavelengths, thus an integer number of crests 614 and troughs 616. Adjacent turns 604 may be nested with one another such that adjacent turns 604 are locally parallel with one another. Thus, the wave pattern of adjacent turns 604 may be in phase with one another.

As shown in FIG. 7, adjacent coil windings or turns 604 may be connected to each other at discrete locations. For example, adjacent coil turns 604 may be welded or soldered to one another at discrete locations or welds 606 along the length of the coil 600. Welding or soldering adjacent coil turns 604 at discrete locations or welds 606 may enhance the flexibility and/or torsional properties of the coil 600. For example, welding of adjacent coil turns 604 may increase the torsional rigidity and torque transmitting properties of the coil 600 without sacrificing the flexibility characteristics of the coil 600. The welds 606 between adjacent coil windings or turns 604 may transfer torsional forces along the coil 600 while the coil 600 retains its flexibility.

In some embodiments, such as that shown in FIG. 7, each turn 604 of the coil 600 may be fixed to an adjacent coil turn 604 at two or more discrete locations or welds 606. In other words, each turn 604 of the coil 600 may be welded or soldered to an adjacent turn 604 at two, three, four, five, six or more discrete locations or welds 606 within a 360 degree revolution of the coil filament 602. Any 360 degree revolution of the filament 602 may be considered a turn 604. The pattern of welds 606 of the coil 600 may be any desired pattern, including those patterns expressly disclosed herein regarding other exemplary coils. Thus, in the interest of brevity, further discussion of possible weld patterns will not be provided.

Figure 8:
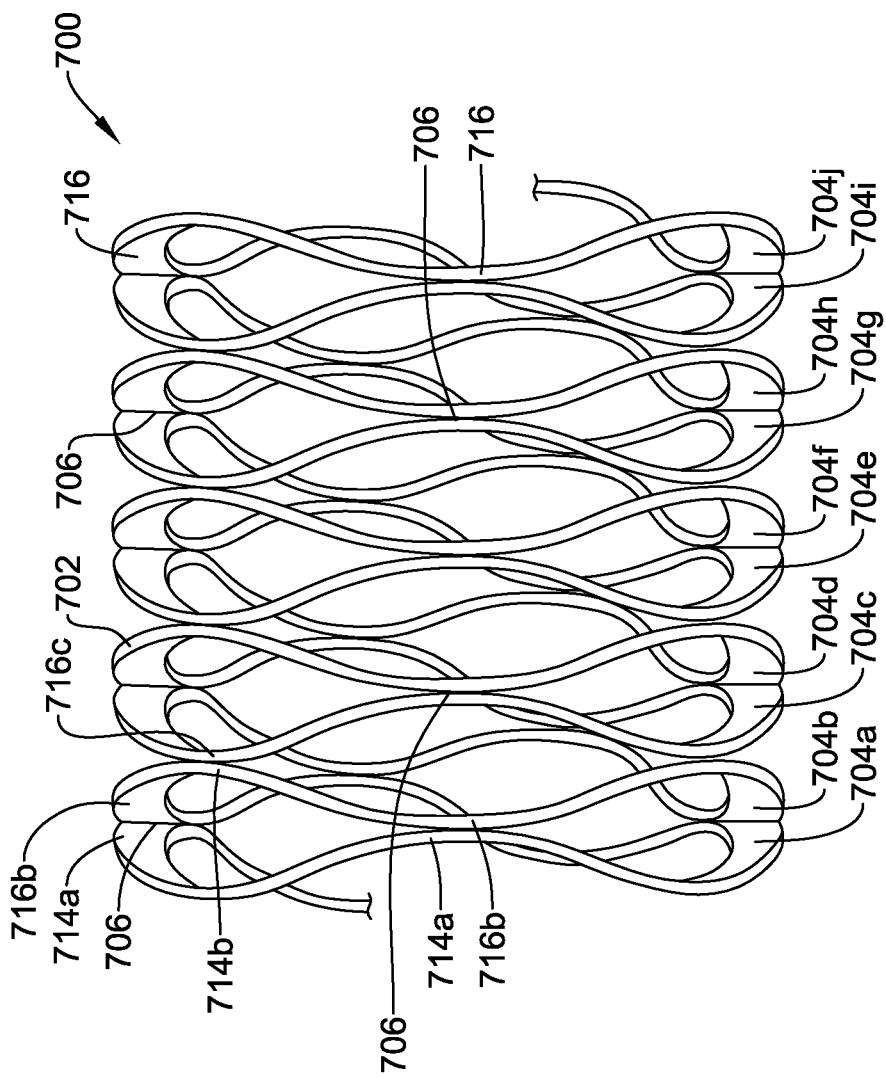
FIG. 8 illustrates an exemplary crest-to-crest wave wound coil.

A crest-to-crest wave wound coil 700 having a longitudinal axis is shown in FIG. 8. The crest-to-crest wave wound coil 700 may include a filament 702 helically wound around the longitudinal axis of the coil 700 to form a plurality of turns or windings 704. As shown in FIG. 8, the filament 702 may be a flat ribbon filament, however, in other embodiments the filament 702 may be a round wire filament. In some embodiments the flat ribbon may be edge wound. In other words, when a cross-section of the flat ribbon filament 7902 is taken, the radial dimension (thickness) of the ribbon filament 702 is greater than the longitudinal dimension (width) of the ribbon filament 702. In other embodiments, the radial dimension (thickness) of the ribbon filament 702 is less than or equal to the longitudinal dimension (width) of the ribbon filament 702. The pitch of adjacent turns 704 of the coil 700 may be tightly wrapped so that each turn 704 touches the succeeding turn 704 or the pitch may be set such that the coil 700 is wrapped in an open fashion, leaving a gap between adjacent turns 704 of the coil 700. A single turn or winding 704 of the filament 702 of the coil 700 is a 360 degree revolution of the filament 702 about the longitudinal axis of the coil 700.

Each turn 704 may include a wave pattern of high periods and low periods. The orthogonal distance between the peak deviation of the high periods and/or low periods and the imaginary base line of the wave is considered the amplitude of the wave. Each turn 704 may include two or more crests 714 and one or more troughs 716 of a wave pattern extending around the circumference of the coil 700. In an exemplary embodiment, a turn 704 may include two crests 714 and three troughs 716, while an immediately preceding and/or following turn 704 may include three crests 714 and two troughs 716. However, in other embodiments, each turn 704 may include any desired number of crests 714 and troughs 716. A wavelength is considered one complete cycle of the wave pattern. A standard crest-to-crest wave wound coil would have an odd integer multiple of ½ wavelengths per turn 704 of the filament 702. In other words, each winding or turn 704 of the filament 702 would have an integer number of wavelengths plus one-half a wavelength. Thus, each turn 704 would include a partial wavelength of the wave pattern. Thus, the crests 714 of adjacent turns 704 may be offset one-half wavelength from one another such that the crests 714a of a first turn 704a are longitudinally aligned and/or in contact with the troughs 716b of a second turn 704b. Likewise, the crests 714b of the second turn 704b may be aligned and/or in contact with the troughs 716c of a third turn 704c, etc. Thus, the wave pattern of any given turn 704 is half a wavelength out of phase with the waves of the turns immediately on either side of the given turn 704, so that the crests of the given turn 704 contact the troughs 716 of the adjacent turns 704. As shown in FIG. 8, the crests 714 of a first turn 704a are located out of phase with the crests 714 of a second turn 704b immediately adjacent the first turn 704a.

As shown in FIG. 8, adjacent coil windings or turns 704 may be connected to each other at discrete locations. For example, adjacent coil turns 704 may be welded or soldered to one another at discrete locations or welds 706 along the length of the coil 700. Welding or soldering adjacent coil turns 704 at discrete locations or welds 706 may enhance the flexibility and/or torsional properties of the coil 700. For example, welding of adjacent coil turns 704 may increase the torsional rigidity and torque transmitting properties of the coil 700 without sacrificing the flexibility characteristics of the coil 700. The welds 706 between adjacent coil windings or turns 704 may transfer torsional forces along the coil 700 while the coil 700 retains its flexibility.

In some embodiments, such as that shown in FIG. 8, each turn 704 of the coil 700 may be fixed to an adjacent coil turn 704 at two or more discrete locations or welds 706. In other words, each turn 704 of the coil 700 may be welded or soldered to an adjacent turn 704 at two, three, four, five, six or more discrete locations or welds 706 within a 360 degree revolution of the coil filament 702. Any 360 degree revolution of the filament 702 may be considered a turn 704.

As shown in FIG. 8, adjacent coil windings or turns 704 are welded or soldered together at the contact points where the crests 714 of a first turn 704 contact the troughs 716 of a second turn 704. Likewise, the crests 714 of the second turn 704 may be welded or soldered to the troughs 716 of a third turn 704 where the crests 714 of the second turn contact the troughs 716 of a third turn 704, etc.

One exemplary soldering technique which may be used to weld or solder adjacent turns 704 of the coil 700 together is bulk soldering or wave soldering. A bulk soldering or wave soldering technique, such as the one described herein, may also be used to fix contact points of adjacent coil windings together with solder, as desired. Wave soldering is a large-scale soldering process by which components may be soldered in large volumes. Such a process may be found to be much faster, more reliable and more efficient than the manual soldering of components.

A typical wave soldering process includes three zones and/or steps: a fluxing zone, a preheating zone, and a soldering zone. Some wave soldering processes include a fourth zone, a cleaning zone, subsequent to the soldering zone in some circumstances.

In the fluxing zone, flux may be applied to the component. Excess flux may be removed as desired. In the preheating zone, the component, as well as the flux applied to the component, is heated to an elevated temperature. Heating the component and flux activates the flux and also prevents thermal shock of the component. The component may then be brought into contact with a quantity of bulk solder. For example, the component may be dipped in a tank of molten solder, or a stream of molten solder may be poured over the component. By controlling the soldering process, select portions of the component may be soldered together without soldering together other components.

In the case of a coil, such as the coil 700, the coil 700 may be subjected to a quantity of bulk solder. For example, the coil 700 may be dipped in a tank of molten solder, or a stream of molten solder may be poured over the coil 700. Due to surface tension, an amount of solder will tend to wick to the contact locations where a first turn 704 of the coil 700 contacts an adjacent turn 704 of the coil 700. At other locations, the solder is unable to bridge the distance between adjacent turns 704 of the coil, thus the excess solder flows off the coil 700 and back to a bulk reservoir of solder. In some embodiments excess solder may be repelled from the coil 700. Only solder at the contact locations between adjacent coil windings or turns 704 remains on the coil 700. It can be seen that multiple contact locations between crests 714 and troughs 716 of turns 704 of a coil 700 may simultaneously soldered with such a process.

In other embodiments, an adhesive application may be used to bond contact locations between crests 714 and troughs 716 of turns 704 of a coil 700. For example, an adhesive may be applied to the coil 700 such that the adhesive is retained at the contact locations between crests 714 and troughs 716 of turns 704 of the coil 700, while the adhesive is not retained at other locations. Similar to the wave soldering technique described above, the coil 700 may be subjected to a quantity of bulk adhesive. For example, the coil 700 may be dipped in a tank of liquefied adhesive, or a stream of liquefied adhesive may be poured or sprayed over the coil 700. Thus, it can be seen that multiple contact locations between crests 714 and troughs 716 of turns 704 of a coil 700 may simultaneously bonded together with such a process.

Figure 9:
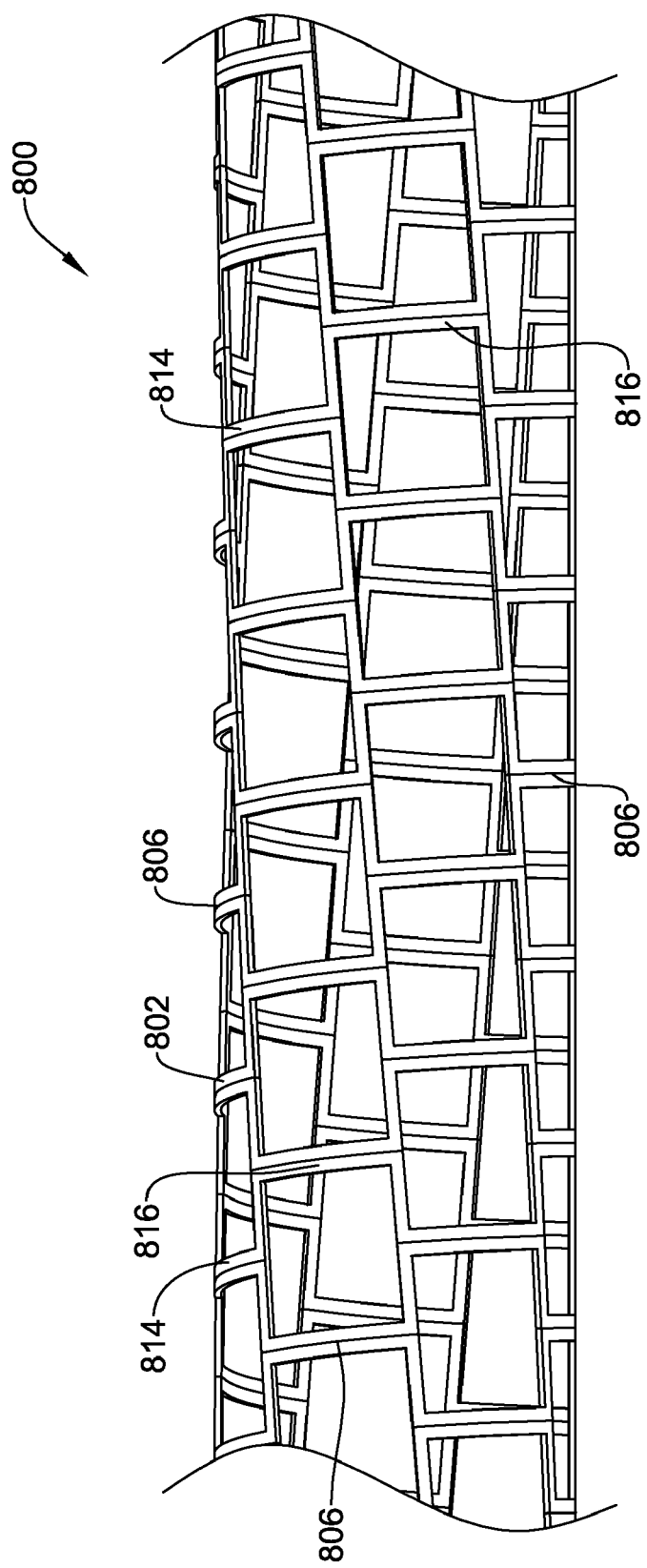
FIG. 9 illustrates an exemplary square-wave wave wound coil.

A square-wave wave wound coil 800 is shown in FIG. 9. The square-wave wave wound coil 800 may include a filament 802 helically wound around the longitudinal axis of the coil 800 to form a plurality of turns or windings 804. As shown in FIG. 9, the filament 802 may be a flat ribbon filament. In some embodiments, the flat ribbon may be an edge wound ribbon filament. However, in other embodiments the filament 802 may be a round wire filament, or a filament with another cross-sectional shape.

As shown in FIG. 9, adjacent coil windings or turns 804 may be connected to each other at discrete locations. For example, adjacent coil turns 804 may be welded or soldered to one another at discrete locations or welds 806 along the length of the coil 800. Welding or soldering adjacent coil turns 804 at discrete locations or welds 806 may enhance the flexibility and/or torsional properties of the coil 800. For example, welding of adjacent coil turns 804 may increase the torsional rigidity and torque transmitting properties of the coil 800 without sacrificing the flexibility characteristics of the coil 800. The welds 806 between adjacent coil windings or turns 804 may transfer torsional forces along the coil 800 while the coil 800 retains its flexibility.

In some embodiments, such as that shown in FIG. 9, each turn 804 of the coil 800 may be fixed to an adjacent coil turn 804 at two or more discrete locations or welds 806. In other words, each turn 804 of the coil 800 may be welded or soldered to an adjacent turn 804 at two, three, four, five, six or more discrete locations or welds 806 within a 360 degree revolution of the coil filament 802. Any 360 degree revolution of the filament 1002 may be considered a turn 804.

Each turn 804 may include a wave pattern of high periods and low periods. As shown in FIG. 9, each turn 804 may include a square wave pattern of upper flat segments 814 and lower flat segments 816. As shown in FIG. 9, adjacent coil windings or turns 804 are welded or soldered together at the contact points where the upper flat segments 814 of a first turn 804 contact the lower flat segments 816 of a second turn 804. Likewise, the upper flat segments 814 of the second turn 804 may be welded or soldered to the lower flat segments 816 of a third turn 804, etc.

Any of the various welding and soldering techniques described herein, including the wave soldering technique described with respect to the coil 700 of FIG. 8, may be used to form welds 806 at discrete contact locations between adjacent turns 804 of the coil 800.

FIGS. 10A-10K illustrate various wave patterns of a wave wound coil which is hypothetically extended out in a flat, planar direction. These representations present the coil as though it had been sliced longitudinally at one radial position and then unrolled or opened along the slice and extended in a planar position. It is noted that these views are for illustrative purposes only.

Figure 10A:
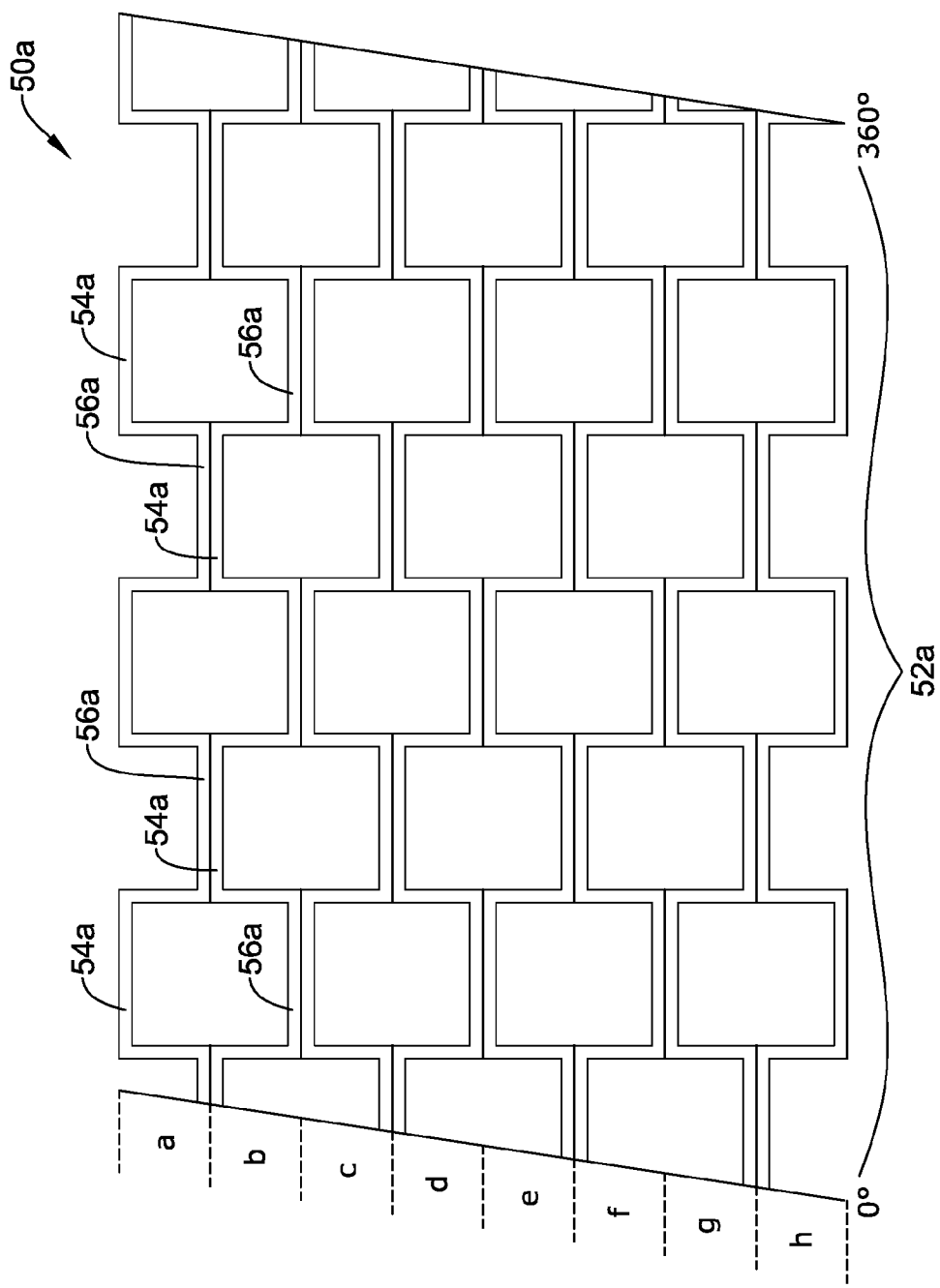
FIGS. 10A-10K illustrate various wave patterns for a wave wound coil.

FIG. 10A illustrates the wave pattern of a square-wave wave wound coil 50a in which successive turns 52a of the coil 50a are one half wavelength out of phase with an immediately preceding turn 52a of the coil 50a. The square-wave wave wound coil 50a may be substantially similar to the coil 800 shown in FIG. 9. Each turn 52a of the coil 50a is designated by one of the letters a-h. It is noted that the end of a turn 52a at the 360 degree point of the figure would join with the end of the next successive turn 52a at the 0 degree point of the figure. The waved segments 52a have a wave pattern of high periods and low periods. As can be seen in FIG. 10A, the upper flat segment 54a of a wave of a turn 52a may contact a lower flat segment 56a of a wave of an adjacent turn 52a. The upper segment 54a may be aligned with and overlap the lower segment 56a of a preceding turn 52a. Adjacent waves may be fixed together at contact points where a first turn 52a of the coil 50a contacts a second turn 52a of the coil 50a, for example by welding or bonding.

Figure 10B:
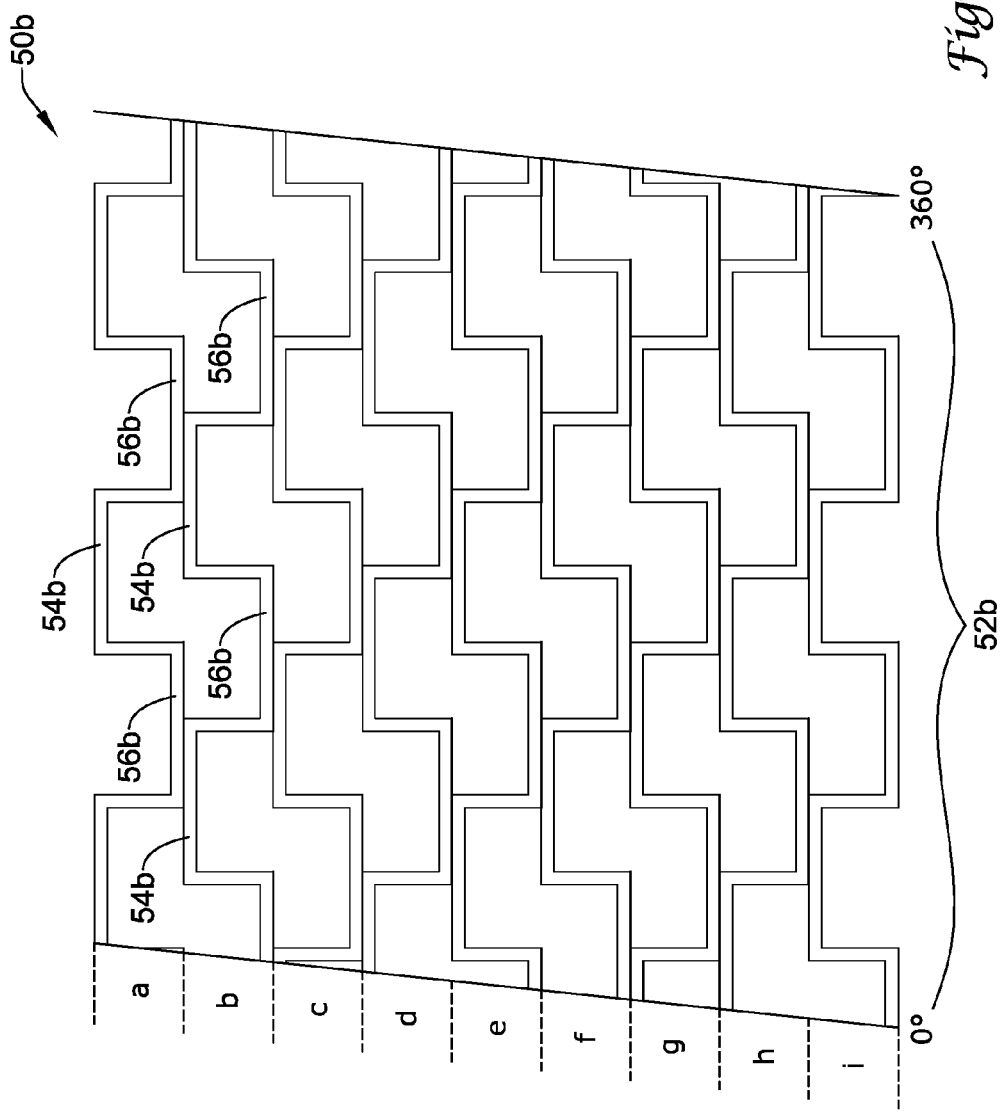

FIG. 10B illustrates the wave pattern of a square-wave wave wound coil 50b in which successive turns 52b of the coil 50b are one quarter wavelength out of phase with an immediately preceding turn 52b of the coil 50b. Each turn 52b of the coil 50b is designated by one of the letters a-i. It is noted that the end of a turn 52b at the 360 degree point of the figure would join with the end of the next successive turn 52b at the 0 degree point of the figure. As can be seen in FIG. 10B, the high period or upper flat segment 54b of a wave of a turn 52b may contact a low period or lower flat segment 56b of a wave of an adjacent turn 52b. The upper segment 54b may half overlap the lower segment 56b of a preceding turn 52b. Adjacent waves may be fixed together at contact points where a first turn 52b of the coil 50b contacts a second turn 52b of the coil 50b, for example by welding or bonding.

Figure 10C:
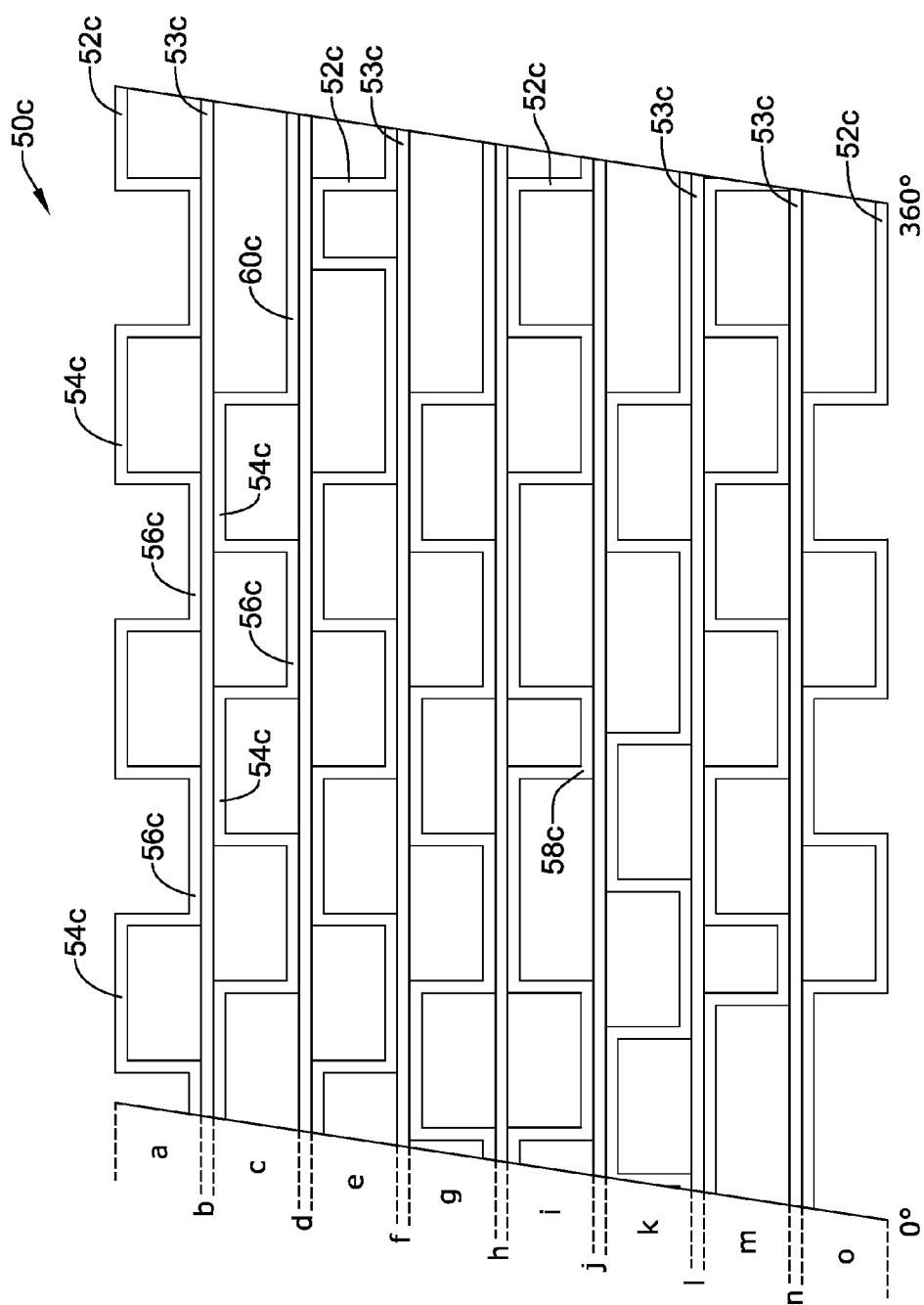

FIG. 10C illustrates the wave pattern of a square-wave wave wound coil 50c in which alternating turns 52c/53c (i.e., every other turn) is non-waved. Each turn 52c/53c of the coil 50c is designated by one of the letters a-o. It is noted that the end of a turn 52c/53c at the 360 degree point of the figure would join with the end of the next successive turn 53c/52c at the 0 degree point of the figure. The waved segments 52c have a wave pattern of high periods and low periods. As can be seen in FIG. 10C, the upper flat segment 54c of a wave of a turn 52c may contact the next successive turn 53c which is non-waved. Similarly, the lower flat segment 56c of a wave of a turn 52c may contact the previous turn 53c which is non-waved. Adjacent turns 52c/53c may be fixed together at contact points where a first turn 52c/53c of the coil 50c contacts a second turn 53c/52c of the coil 50c, for example by welding or bonding. As shown in FIG. 10C, periodic short pulses 58c and/or long pulses 60c in the turns 52c may be included in order to properly position the filament of the coil 50c for the non-waved turns 53c.

Figure 10D:
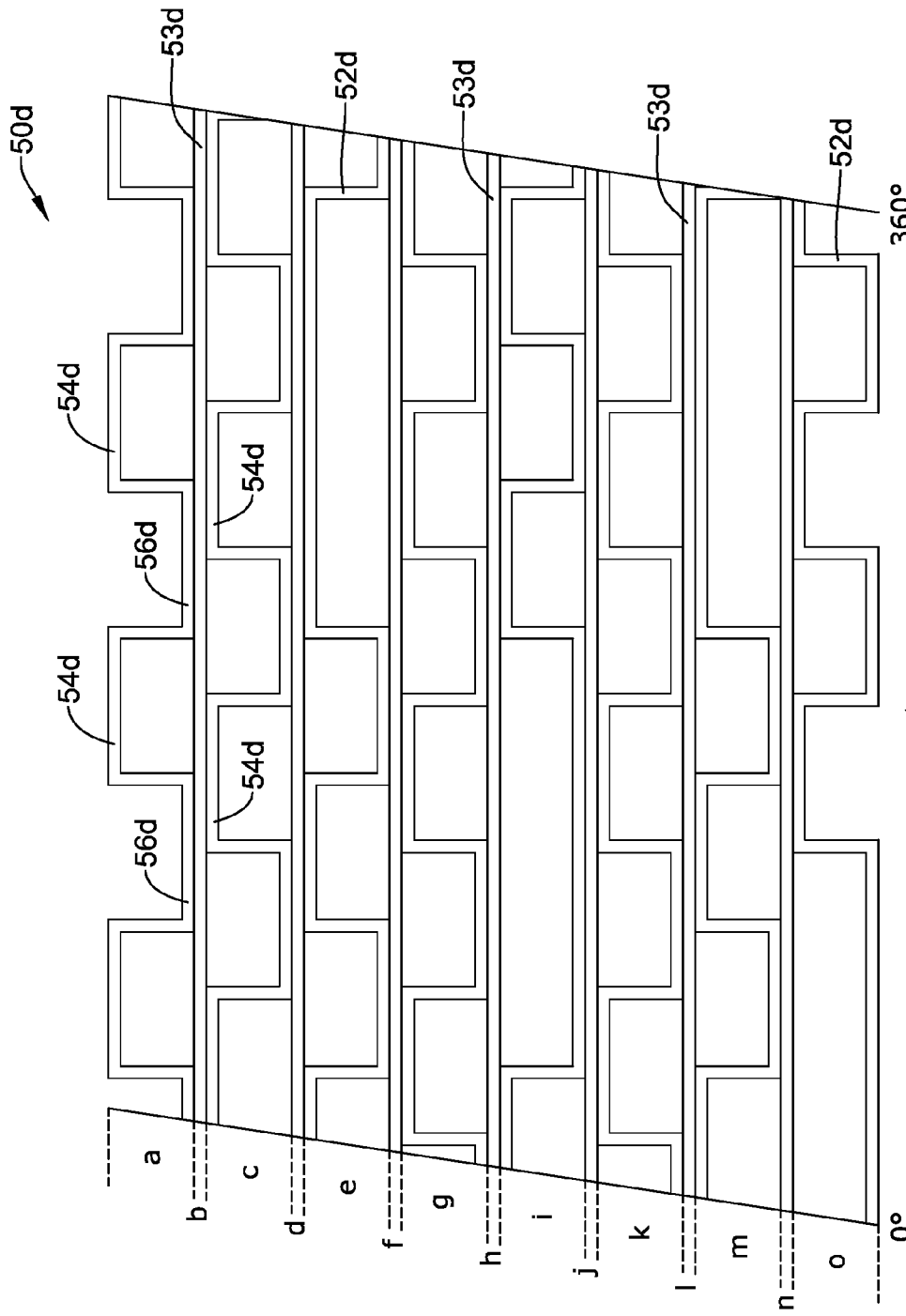

FIG. 10D illustrates the wave pattern of a square-wave wave wound coil 50d in which alternating turns 52d/53d (i.e., every other turn) is non-waved. Each turn 52d/53d of the coil 50d is designated by one of the letters a-o. It is noted that the end of a turn 52d/53d at the 360 degree point of the figure would join with the end of the next successive turn 53d/52d at the 0 degree point of the figure. The waved segments 52d have a wave pattern of high periods and low periods. As can be seen in FIG. 10D, the upper flat segment 54d of a wave of a turn 52d may contact the next successive turn 53d which is non-waved. Similarly, the lower flat segment 56d of a wave of a turn 52d may contact the previous turn 53d which is non-waved. Adjacent turns 52d/53d may be fixed together at contact points where a first turn 52d/53d of the coil 50d contacts a second turn 53d/52d of the coil 50d, for example by welding or bonding. As shown in FIG. 10D, periodically a half wave is skipped in the turns 52d in order to properly position the filament of the coil 50d for the non-waved turns 53d. Thus, in some turns 42d, one or more of the upper segments 54d and/or one or more of the lower segments 56d may have a length greater than the remainder of the upper and/or lower segments 54d/56d of the turn 52d.

Figure 10E:
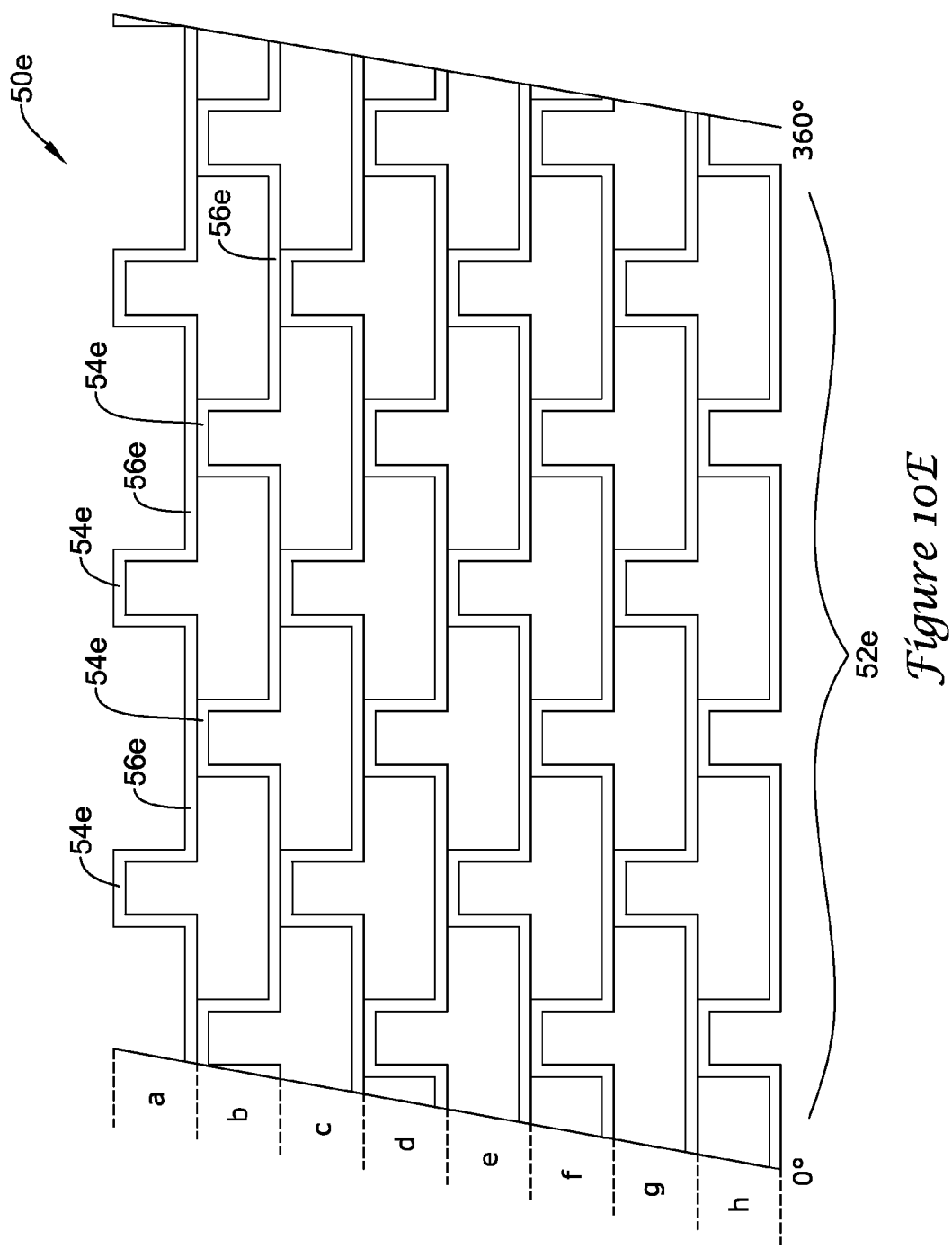

FIG. 10E illustrates the wave pattern of a square-wave wave wound coil 50e which has unequal lengths of upper segments 54e and lower segments 56e of the wave pattern. Each turn 52e of the coil 50e is designated by one of the letters a-h. It is noted that the end of a turn 52e at the 360 degree point of the figure would join with the end of the next successive turn 52e at the 0 degree point of the figure. The waved segments 52e have a wave pattern of high periods and low periods. In FIG. 10E, successive turns 52e of the coil 50e are one half wavelength out of phase with an immediately preceding turn 52e of the coil 50e. Thus, the upper flat segments 54e of every other turn 52e may be longitudinally aligned. The length of the upper segments 54e may be less than the length of the lower flat segments 56e, thus creating a pattern in which the upper segments 54e appear to be extending from an otherwise flat turn 52e. In some embodiments the upper segments 54e may be considered momentary pulses extending from an otherwise flat turn 52e. In some embodiments the upper segments 54e may form about 1% or less, about 2% or less, about 3% or less, about 4% or less, about 5% or less, about 6% or less, about 7% or less, about 8% or less, about 9% or less, about 10% or less, about 15% or less, or about 20% or less of the total wavelength of the wave pattern. As can be seen in FIG. 10E, the upper segment 54e of a wave of a turn 52e may contact a lower segment 56e of a wave of an adjacent turn 52e. Adjacent waves may be fixed together at contact points where a first turn 52e of the coil 50e contacts a second turn 52e of the coil 50e, for example by welding or bonding.

Figure 10F:
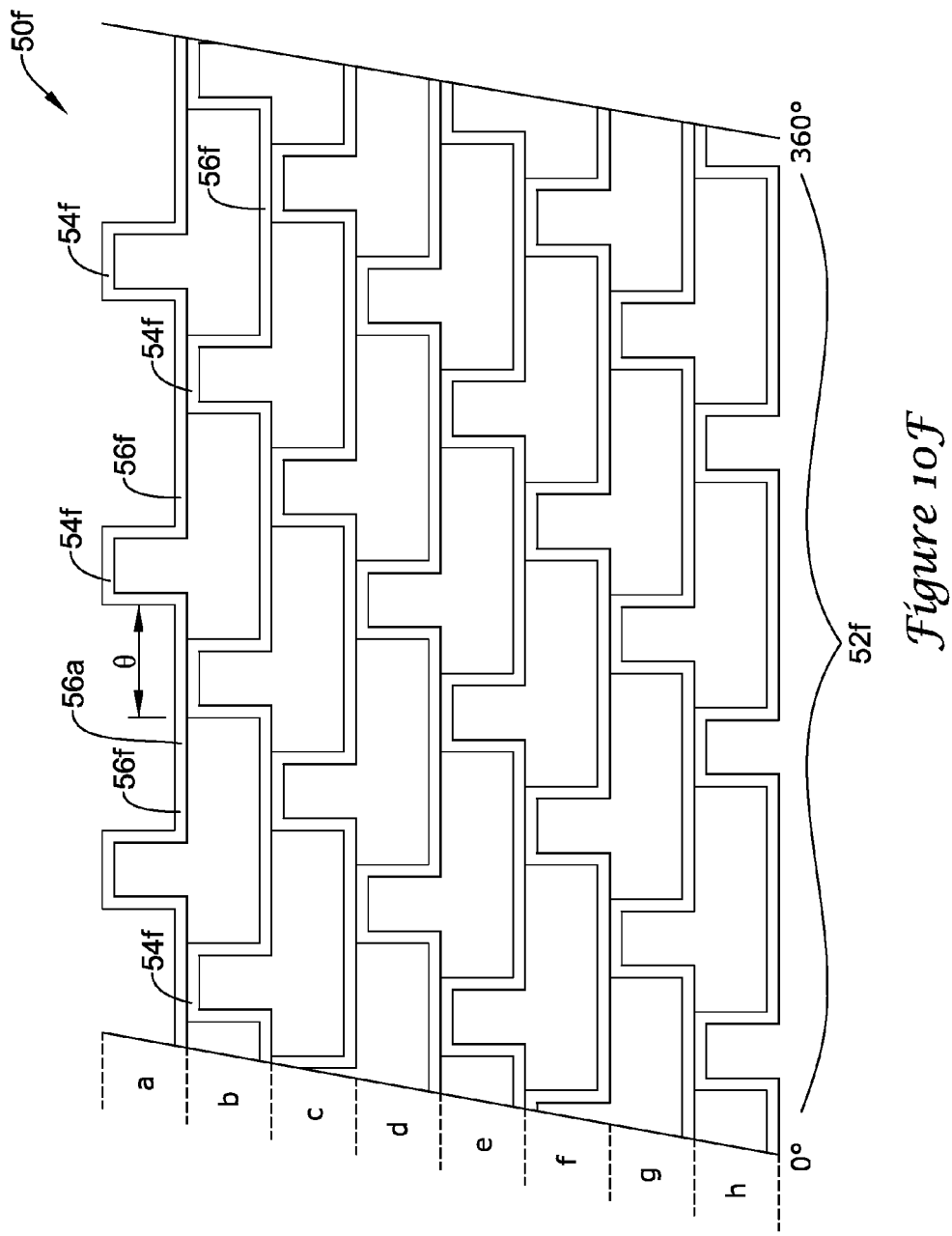

FIG. 10F illustrates the wave pattern of a square-wave wave wound coil 50f which has unequal lengths of upper segments 54f and lower segments 56f of the wave pattern, similar to that of FIG. 10E. Each turn 52f of the coil 50f is designated by one of the letters a-h. In FIG. 10F, successive turns 52f of the coil 50f are phase shifted by an angle θ such that the upper segments 54f of successive turns 52f are not longitudinally aligned with one other. In other words, the upper segments 54f, within a localized area, do not fall at the same polar angle as adjacent upper segments 54f. In some embodiments the upper segments 54f of a given turn 52f may be shifted about $\frac{1}{180}^{th}$ wavelength, about $\frac{1}{72}^{nd}$ wavelength, about $\frac{1}{36}^{th}$ wavelength, or about $\frac{1}{18}^{th}$ wavelength from the upper segments 54f of a preceding and/or successive turn 52f. This pattern provides the coil with isotropic bending characteristics. The length of the upper segments 54f may be less than the length of the lower segments 56f, thus creating a pattern in which the upper segments 54f appear to be extending from an otherwise flat turn 52f. In some embodiments the upper segments 54f may be considered momentary pulses extending from an otherwise flat turn 52f. In some embodiments the upper segments 54f may form about 1% or less, about 2% or less, about 3% or less, about 4% or less, about 5% or less, about 6% or less, about 7% or less, about 8% or less, about 9% or less, about 10% or less, about 15% or less, or about 20% or less of the total wavelength of the wave pattern. As can be seen in FIG. 10F, the upper segment 54f of a wave of a turn 52f may contact a lower segment 56f of a wave of an adjacent turn 52f. Adjacent waves may be fixed together at contact points where a first turn 52f of the coil 50f contacts a second turn 52f of the coil 50f, for example by welding or bonding.

Figure 10G:
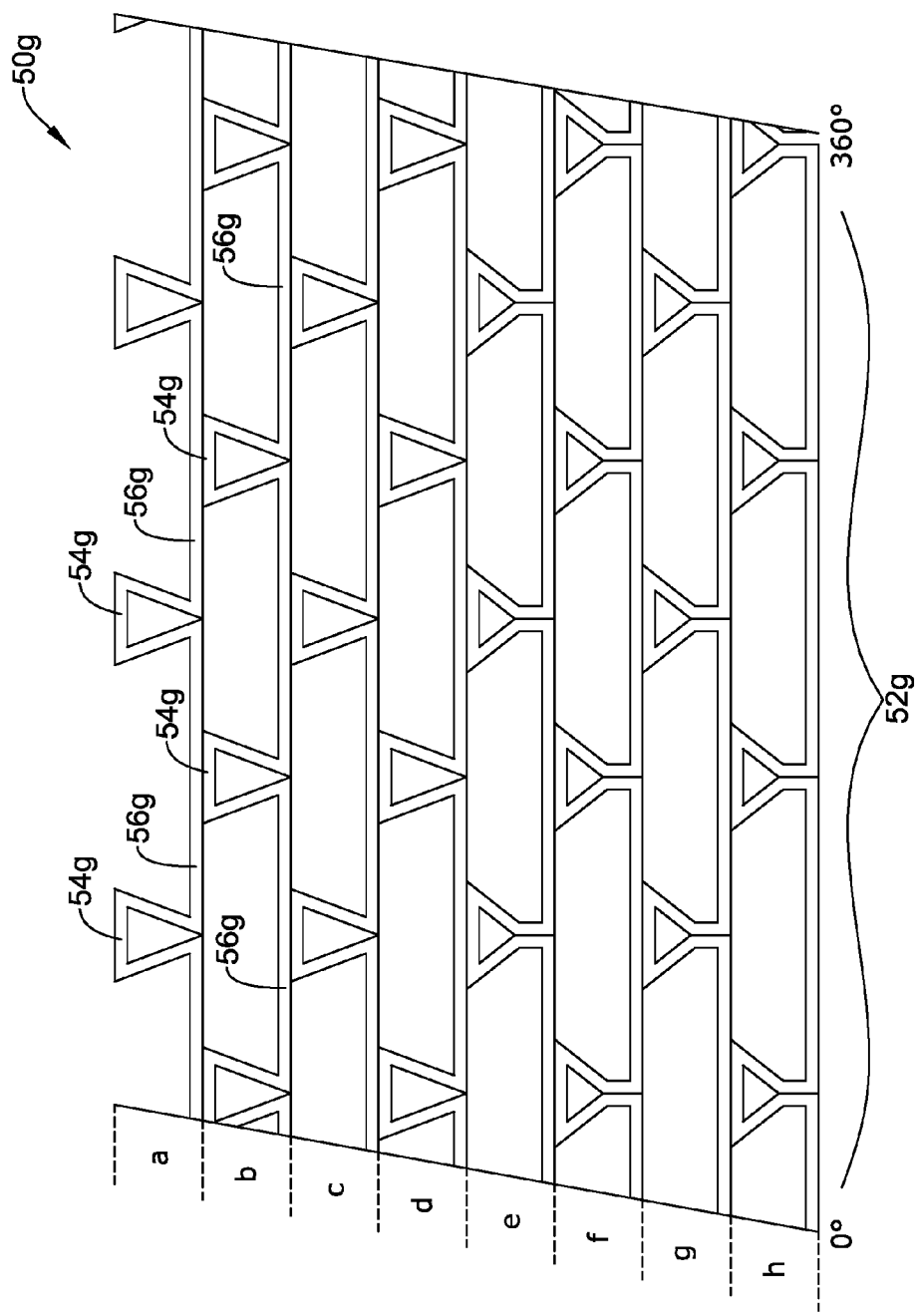

FIG. 10G illustrates the wave pattern of a modified square-wave wave wound coil 50g which has unequal lengths of upper segments 54g and lower segments 56g of the wave pattern, similar to the wave pattern of FIG. 10E. Each turn 52g of the coil 50g is designated by one of the letters a-h. It is noted that the end of a turn 52g at the 360 degree point of the figure would join with the end of the next successive turn 52g at the 0 degree point of the figure. In FIG. 10G, successive turns 52g of the coil 50g are one have wavelength out of phase with an immediately preceding turn 52g of the coil 50g. Thus, the upper segments 54g of every other turn 52g may be longitudinally aligned. The length of the upper segments 54g may be less than the length of the lower segments 56g, thus creating a pattern in which the upper segments 54g appear to be extending from an otherwise flat turn 52g. In some embodiments the upper segments 54g may be considered momentary pulses extending from an otherwise flat turn 52g. In some embodiments the upper segments 54g may form about 1% or less, about 2% or less, about 3% or less, about 4% or less, about 5% or less, about 6% or less, about 7% or less, about 8% or less, about 9% or less, about 10% or less, about 15% or less, or about 20% or less of the total wavelength of the wave pattern. The wave pattern of FIG. 10G may not have square or orthogonal rising segments and/or falling segments as does the wave pattern of FIG. 10E. FIG. 10G shows two separate variations in which the upper segments 54g may have an inverted triangular shape extending from the lower segments 56g of a turn 52g of the coil 50g. A first variation is illustrated in turns a-d of the coil 50g, and a second variation is illustrated in turns e-h of the coil 50g. A coil having this wave pattern may include upper segments 54g of the first variation, may include upper segments 54g of the second variation, or may include upper segments 54g of a combination of the first variation and the second variation. As can be seen in FIG. 10G, the upper segment 54g of a wave of a turn 52g may contact a lower segment 56g of a wave of an adjacent turn 52g. Adjacent waves may be fixed together at contact points where a first turn 52g of the coil 50g contacts a second turn 52g of the coil 50g, for example by welding or bonding.

Figure 10H:
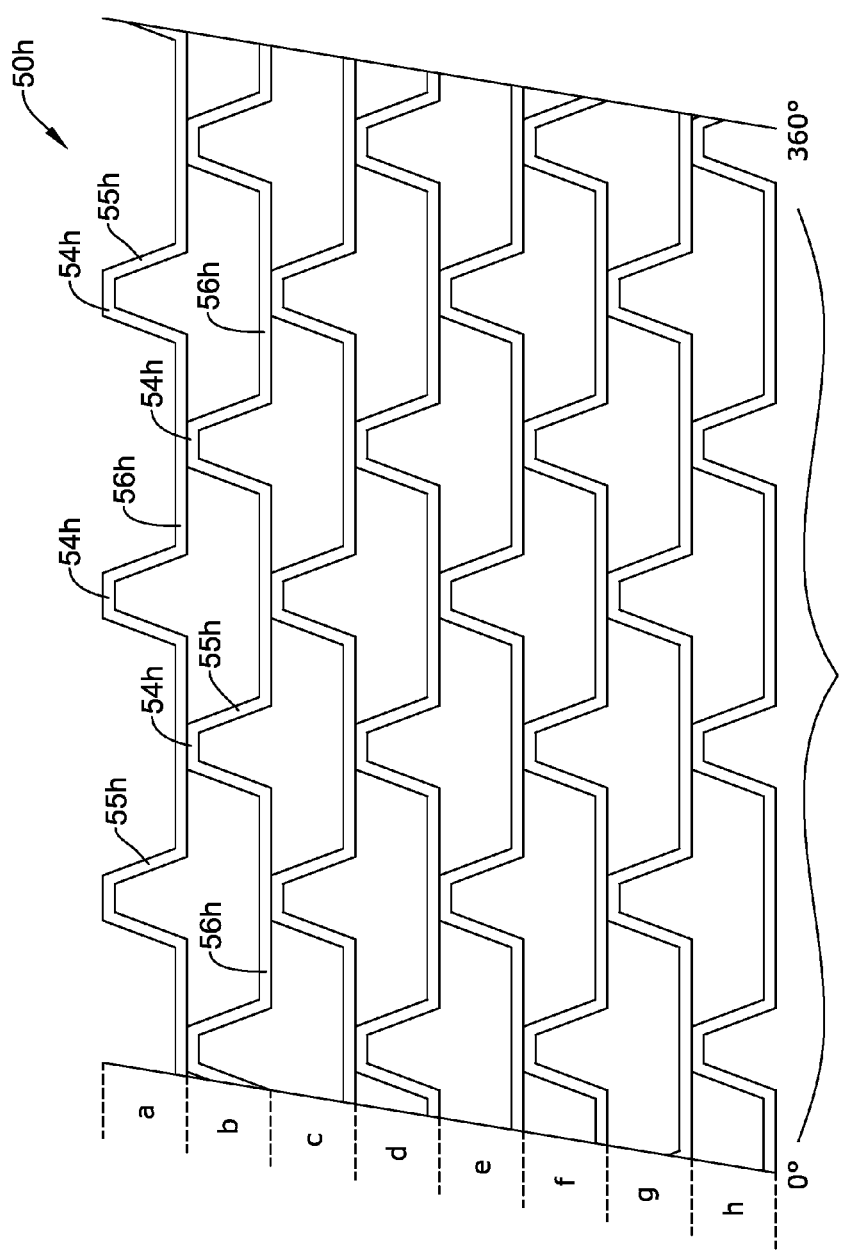

FIG. 10H illustrates the wave pattern of a trapezoidal-wave wave wound coil 50h which has unequal lengths of upper segments 54h and lower segments 56h of the wave pattern. The transition portions 55f between the upper segments 54h and the lower segments 56h are set at an oblique angle to the upper segments 54h and lower segments 56h, thus forming a trapezoidal wave pattern. Each turn 52h of the coil 50h is designated by one of the letters a-h. It is noted that the end of a turn 52h at the 360 degree point of the figure would join with the end of the next successive turn 52h at the 0 degree point of the figure. In FIG. 10H, successive turns 52h of the coil 50h are one half wavelength out of phase with an immediately preceding turn 52h of the coil 50h. Thus, the upper segments 54h of every other turn 52h may be longitudinally aligned. The length of the upper segments 54h may be less than the length of the lower segments 56h, thus creating a pattern in which the upper segments 54h appear to be extending from an otherwise flat turn 52h with the angled transition segments 55h. In some embodiments the upper segments 54h may be considered momentary pulses extending from an otherwise flat turn 52h. In some embodiments the upper segments 54h may form about 1% or less, about 2% or less, about 3% or less, about 4% or less, about 5% or less, about 6% or less, about 7% or less, about 8% or less, about 9% or less, about 10% or less, about 15% or less, about 20% or less, about 30% or less or about 40% or less of the total wavelength of the wave pattern. As can be seen in FIG. 10H, the upper segment 54h of a wave of a turn 52h may contact a lower segment 56h of a wave of an adjacent turn 52h. Adjacent waves may be fixed together at contact points where a first turn 52h of the coil 50h contacts a second turn 52h of the coil 50h, for example by welding or bonding.

Figure 10I:
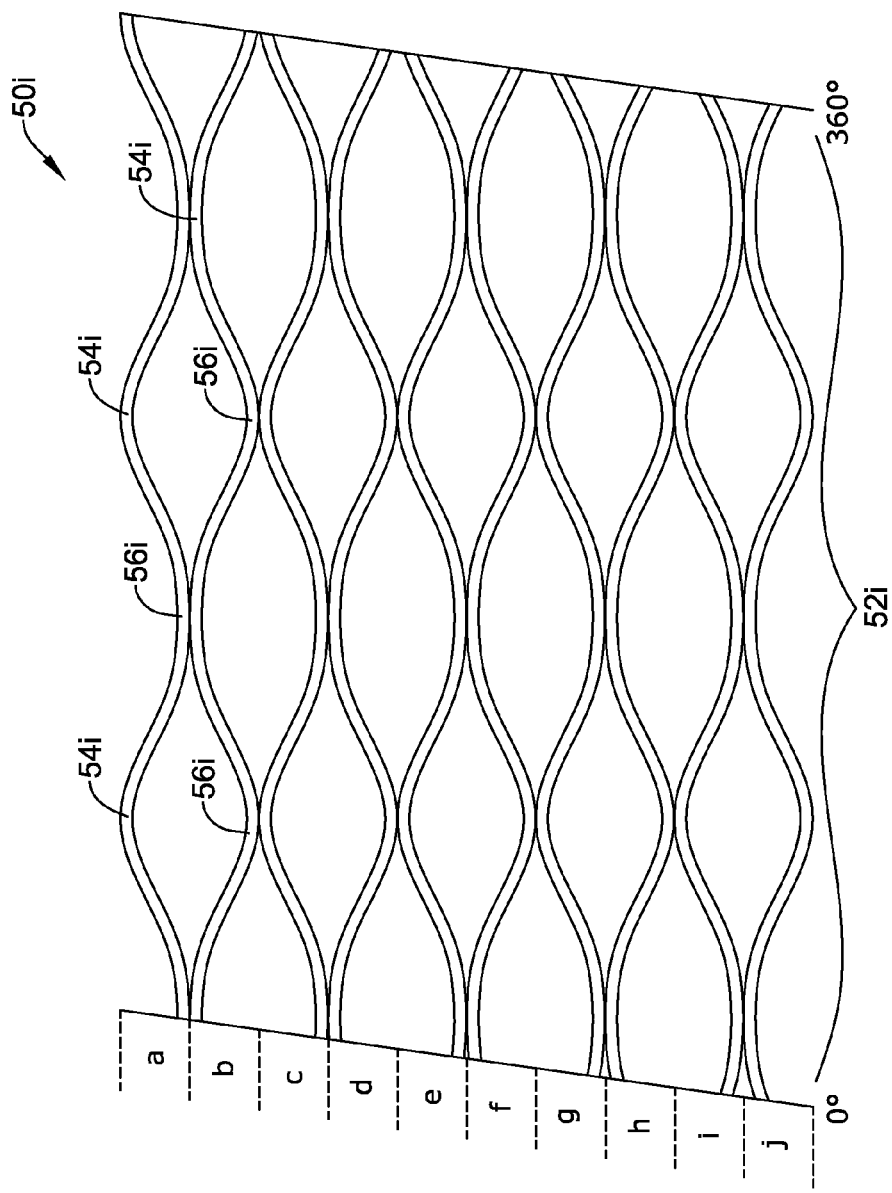

FIG. 10I illustrates the wave pattern of a crest-to-crest wave wound coil 50i which includes crests 54i and troughs 56i of the wave pattern. Each turn 52i of the coil 50i is designated by one of the letters a-l. It is noted that the end of a turn 52i at the 360 degree point of the figure would join with the end of the next successive turn 52i at the 0 degree point of the figure. In FIG. 10I, successive turns 52i of the coil 50i are one half wavelength out of phase with an immediately preceding turn 52i of the coil 50i. Thus, the crests 54i of every other turn 52i may be longitudinally aligned. Furthermore, the crests 54i of each turn 52i may be longitudinally aligned with the troughs 56i of a successive turn 52i. As can be seen in FIG. 10I, the crest 54i of a wave of a turn 52i may contact a trough 56i of a wave of an adjacent turn 52i. Similarly, the trough 56i of a wave of a turn 52i may contact a crest 54i of a wave of an adjacent turn 52i. Adjacent waves may be fixed together at contact points where a first turn 52i of the coil 50i contacts a second turn 52i of the coil 50i, for example by welding or bonding.

Figure 10J:
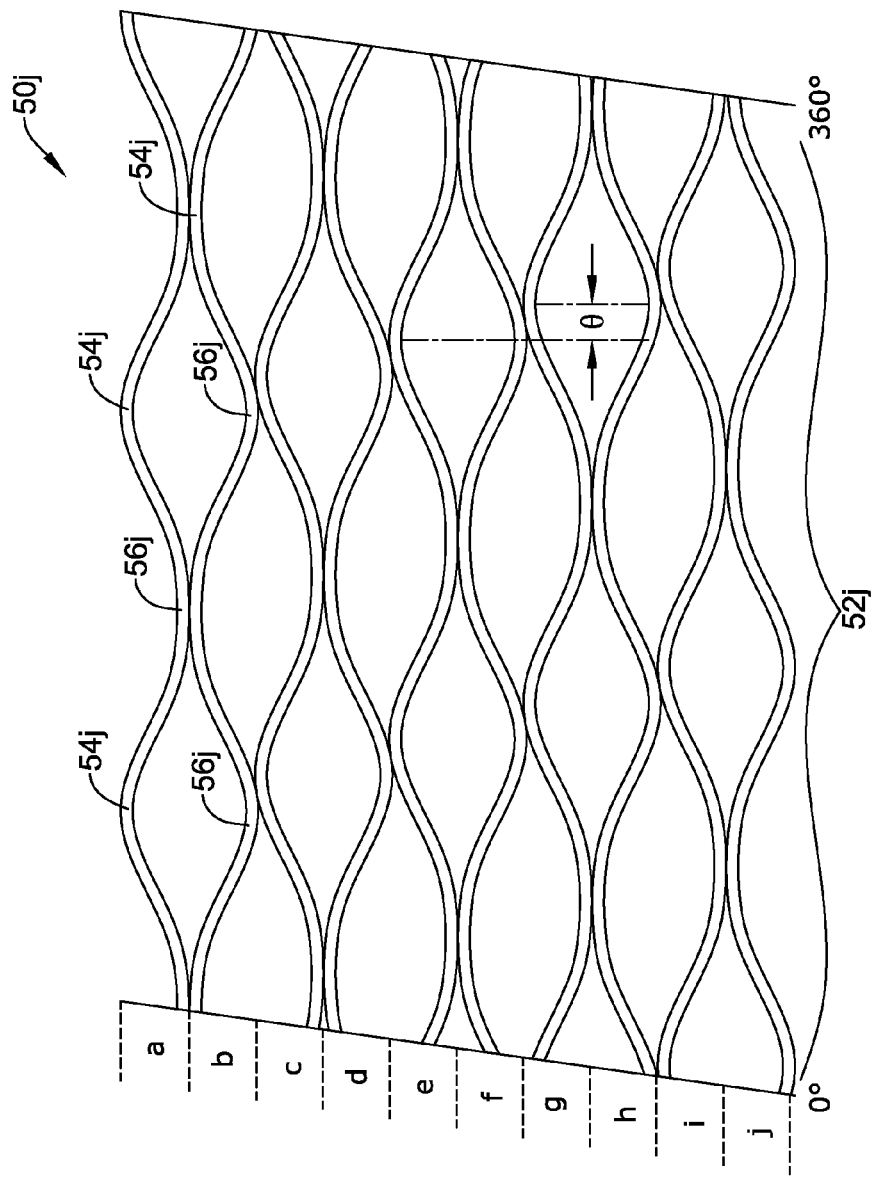

FIG. 10J illustrates the wave pattern of a crest-to-crest wave wound coil 50j which includes crests 54j and troughs 56j of the wave pattern. Each turn 52j of the coil 50j is designated by one of the letters a-l. It is noted that the end of a turn 52j at the 360 degree point of the figure would join with the end of the next successive turn 52j at the 0 degree point of the figure. In FIG. 10J, successive turns 52j of the coil 50j are phase shifted by an angle θ such that the crests 54j of successive turns 52j are not longitudinally aligned with one other. In other words, the crests 54j, within a localized area, do not fall at the same polar angle as crests 54j of an adjacent turn. In some embodiments the crests 54j of a given turn 52j may be shifted about $1/180^{th}$ wavelength, about $1/72^{nd}$ wavelength, about $1/36^{th}$ wavelength, or about $1/18^{th}$ wavelength from the crests 54j of a preceding and/or successive turn 52j. This pattern provides the coil with isotropic bending characteristics. Thus, the crests 54j of every other turn 52j may not be longitudinally aligned. As can be seen in FIG. 10J, the crest 54j of a wave of a turn 52j may contact a trough 56j of a wave of an adjacent turn 52j. Similarly, the trough 56j of a wave of a turn 52j may contact a crest 54j of a wave of an adjacent turn 52j. Adjacent waves may be fixed together at contact points where a first turn 52j of the coil 50j contacts a second turn 52j of the coil 50j, for example by welding or bonding.

Figure 10K:
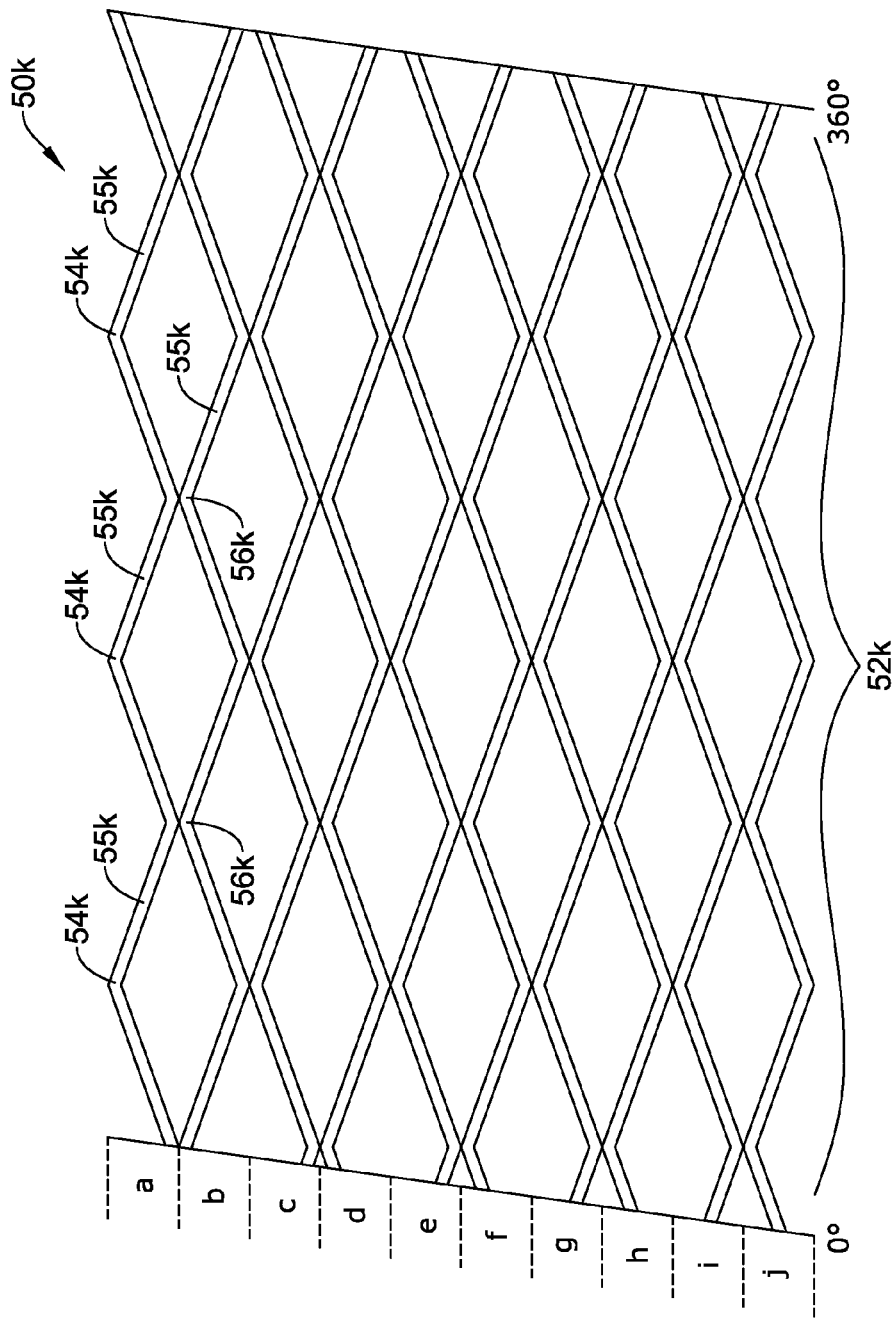

FIG. 10K illustrates the wave pattern of a diamond-wave wave wound coil 50k which includes high periods and low periods. The wave pattern includes upper points 54k and lower points 56k. The transition portions 55k between the upper points 54k and the lower points 56k are angled between the upper points 54k and lower points 56k, thus forming a diamond wave pattern. Each turn 52k of the coil 50k is designated by one of the letters a-l. It is noted that the end of a turn 52k at the 360 degree point of the figure would join with the end of the next successive turn 52k at the 0 degree point of the figure. In FIG. 10K, successive turns 52k of the coil 50k are one half wavelength out of phase with an immediately preceding turn 52k of the coil 50k. Thus, the upper points 54k of every other turn 52k may be longitudinally aligned. Furthermore, the upper points 54k of each turn 52k may be longitudinally aligned with the lower points 56k of a successive turn 52k. As can be seen in FIG. 10K, the upper point 54k of a wave of a turn 52k may contact a lower point 56k of a wave of an adjacent turn 52k. Similarly, the lower point 56k of a wave of a turn 52k may contact an upper point 54k of a wave of an adjacent turn 52k. Adjacent waves may be fixed together at contact points where a first turn 52k of the coil 50k contacts a second turn 52k of the coil 50k, for example by welding or bonding.

Although some exemplary wave patterns have been illustrated herein, additional wave patterns may also be possible. Furthermore, in some embodiments the wavelength, amplitude, wave form, and/or phase shift of a wave pattern can be varied along at least a portion of the length of a coil.

Figure 11:
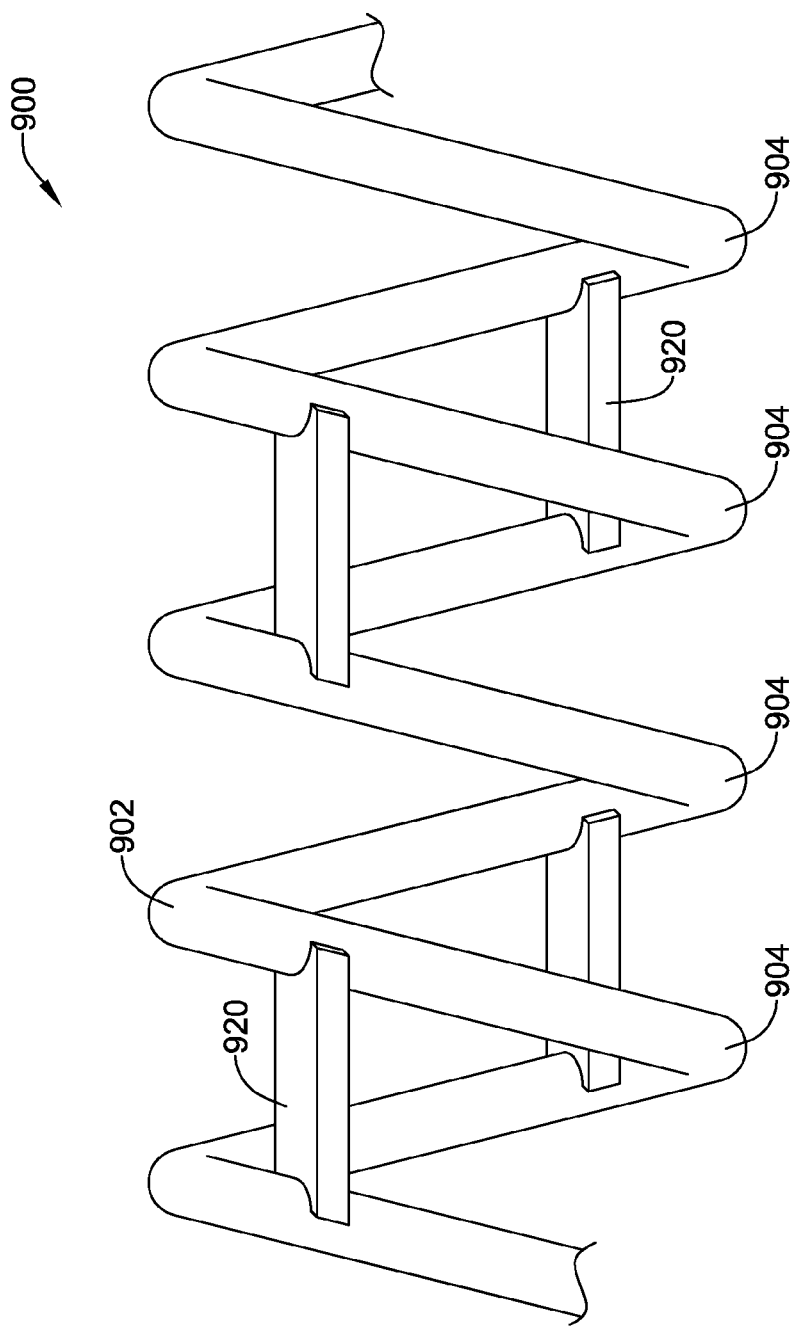
FIG. 11 is a perspective view of another illustrative coil.

Another embodiment of a coil 900 is shown in FIG. 11. The coil 900 may include a filament 902 helically wound around the longitudinal axis of the coil 900 to form a plurality of turns or windings 904. As shown in FIG. 11, the filament 902 may be a round wire filament. However, in other embodiments the filament 902 may be a flat ribbon filament, or a filament with another cross-sectional shape.

As shown in FIG. 11, adjacent coil windings or turns 904 may be connected to each other at discrete locations. In some embodiments, each turn 904 of the coil 900 may be fixed to an adjacent coil turn 904 at two or more discrete locations within a 360 degree revolution of the coil filament 902. For example, the coil 900 may include a plurality of spacers 920 positioned between adjacent turns 904 of the coil 900. Spacers 920 may be placed between adjacent turns 904 during formation of the coil 900, or the spacers 920 may be placed between adjacent turns 904 subsequent to formation of the coil 900. The pattern of spacers 920 of the coil 900 may be any desired pattern, including those patterns expressly disclosed herein regarding welds of other exemplary coils. Thus, in the interest of brevity, further discussion of possible spacer 920 patterns will not be provided.

The spacers 920 may be fixed to the adjacent turns 904 in any known way. For example, the spacers 920 may be welded, crimped, swaged, adhered or otherwise fixed to the adjacent turns 904 of the coil 900. In some embodiments, the spacers 920 may be reflowed by the application of heat (e.g., infrared (IR), convection, vapor phase, ultrasonic, friction, etc.) to fix the spacers 920 to the filament 902 to form a welded coil structure. The spacers 920 may be spaced about and fixed to the coil 900 in any desired pattern such that torsional forces may be transmitted along the coil 900 without compromising the flexibility of the coil 900. The spacers 920 may space adjacent turns 904 of the coil 900 apart from one another, leaving a gap 908 between adjacent turns 904.

In some embodiments, such as that shown in FIG. 11, each turn 904 of the coil 900 may be fixed to an adjacent coil turn 904 at two or more discrete locations with spacers 920. In other words, each turn 904 of the coil 900 may be attached to an adjacent turn 904 at two, three, four, five, six or more discrete locations with spacers 920 within a 360 degree revolution of the coil filament 902. Any 360 degree revolution of the filament 902 may be considered a turn 904.

The bending characteristics of the coil 900 may be controlled, at least in part, by the position of the spacers 920. For example, the position of the spacers 920 may impart isotropic bending and/or anisotropic bending characteristics on the coil 900. Isotropic bending indicates that the bending stiffness of the coil 900 is uniform in all bending planes parallel to the longitudinal axis of the coil 900, and anisotropic bending indicates that there is preferential bending of the coil 900 in one or more bending planes parallel to the longitudinal axis of the coil 900.

Figure 11A:
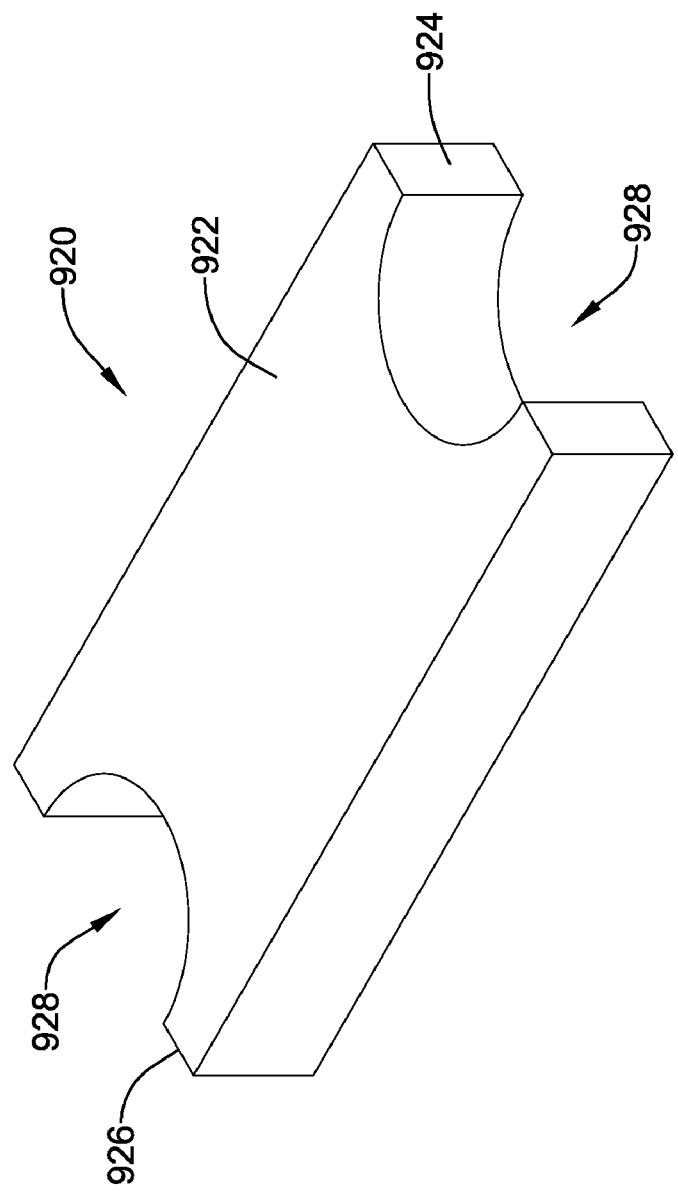
FIG. 11A is a perspective view of a spacer of the coil of FIG. 11.

An enlarged view of a spacer 920 is shown in FIG. 11A. In some embodiments the spacer 920 may have a dog-bone shape. As shown in FIG. 11A, the spacer 920 may include a body 922 having a first end 924 and an opposite second end 926. Each end 924/926 of the spacer 920 may include a recessed portion 928 sized to receive a portion of the filament 902. For example, in some embodiments the recessed portion 928 may be a semi-circular recess for receiving a portion of a round wire filament. In other embodiments, the recessed portion 928 may be a rectangular or slotted recess for receiving a portion of a flat ribbon filament.

Figure 12:
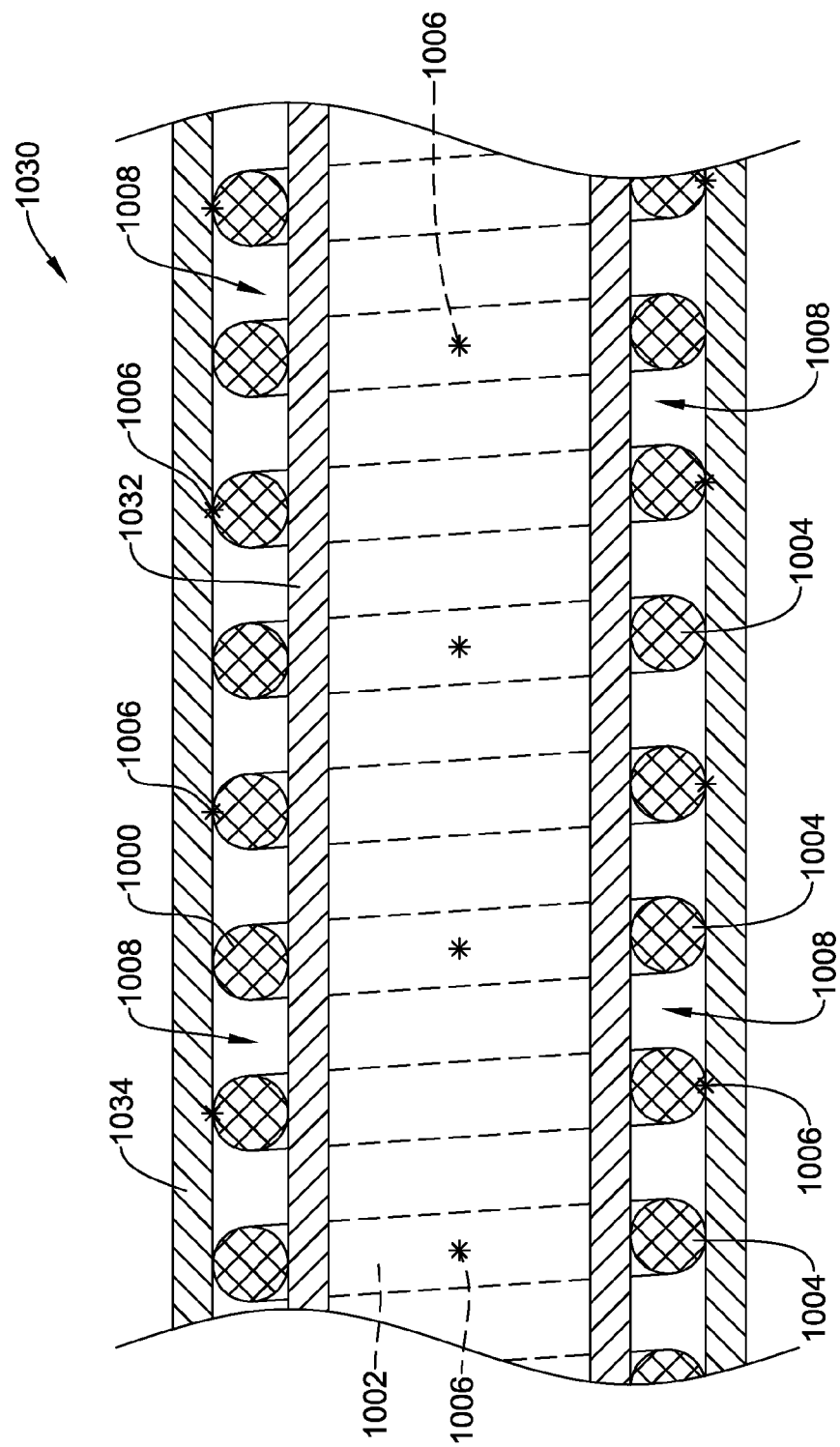
FIG. 12 is a cross-sectional view of a portion of a shaft including a coil.

A cross-section of a shaft 1030 of a medical device (e.g., a guidewire, catheter, etc.) taken along the longitudinal axis of the shaft 1030 is shown in FIG. 12. The shaft 1030 may include an inner tubular member 1032, an outer tubular member 1034 and a coil 1000 interposed between the inner tubular member 1032 and the outer tubular member 1034. The coil 1000, which may be a single filar coil, may be formed of a helically wound filament 1002, which in some embodiments may be a round wire or flat ribbon ranging in dimensions to achieve the desired flexibility. The coil 1000 is illustrated as a round wire coil.

The coil 1000, formed of a wire filament 1002, can be wrapped in a helical fashion around a longitudinal axis by conventional winding techniques to form a plurality of turns or windings 1004. The pitch of adjacent turns 1004 of the coil 1000 may be tightly wrapped so that each turn 1004 of the coil 1000 touches the succeeding turn 1004, or the pitch may be set such that the coil 1000 is wrapped in an open fashion, leaving a gap 1008 between adjacent turns 1004 of the coil 1000. A single turn or winding 1004 of the filament 1002 of the coil 1000 is a 360 degree revolution of the filament 1002.

As shown in FIG. 12, the coil windings or turns 1004 may be fixed to the inner tubular member 1032 and/or the outer tubular member 1034 at a plurality of discrete connection locations 1006. For example, coil turns 1004 of the coil 1000 may be welded, soldered, adhered, bonded, or otherwise fixed to the inner tubular member 1032 and/or the outer tubular member 1034 at discrete connection locations 1006 along the length of the shaft 1030. Fixing the coil turns 1004 to the inner tubular member 1032 and/or the outer tubular member 1034 at discrete connection locations 1006 may enhance the flexibility and/or torsional properties of the shaft 1030. For example, fixing the coil turns 1004 to the inner and/or outer tubular member 1032/1034 may increase the torsional rigidity and torque transmitting properties of the shaft 1030 without sacrificing the flexibility characteristics of the shaft 1030. The discrete connection points 1006 may transfer torsional forces along the coil 1000 while the coil 1000 retains its flexibility.

As shown in FIG. 12, in some embodiments, the inner tubular member 1032 may not be in direct contact with the outer tubular member 1034 as the coil 1000 may provide separation between the inner tubular member 1032 and the outer tubular member 1034. As the inner tubular member 1032 may not be in direct contact with the outer tubular member 1034, a gap 1008 between adjacent turns 1004 of the coil 1000 may be present along the shaft 1030 between the inner tubular member 1032 and the outer tubular member 1034.

In some embodiments, such as that shown in FIG. 12, each turn 1004 of the coil 1000 may be fixed to the inner and/or outer tubular member 1032/1034 at two or more discrete connection locations 1006. In other words, each turn 1004 of the coil 1000 may be fixed to the inner and/or outer tubular member 1032/1034 at two, three, four, five, six or more discrete connection locations 1006 within a 360 degree revolution of the coil filament 1002. Any 360 degree revolution of the filament 1002 may be considered a turn 1004.

As used herein, "discrete connection locations" include connection points which are discontinuous with one another along the shaft 1030. In other words, each discrete connection location 1006 may be discernable from another discrete connection location 1006 by a portion of the coil 1000 which is not fixed to the inner and/or outer tubular member 1032/1034.

The bending characteristics of the shaft 1030 may be controlled, at least in part, by the position of the discrete connection locations 1006. For example, the position of the discrete connection locations 1006 may impart isotropic bending and/or anisotropic bending characteristics on the shaft 1030. Isotropic bending indicates that the bending stiffness of the shaft 1030 is uniform in all bending planes parallel to the longitudinal axis of the shaft 1030, and anisotropic bending indicates that there is preferential bending of the shaft 1030 in one or more bending planes parallel to the longitudinal axis of the shaft 1030.

Figure 13:
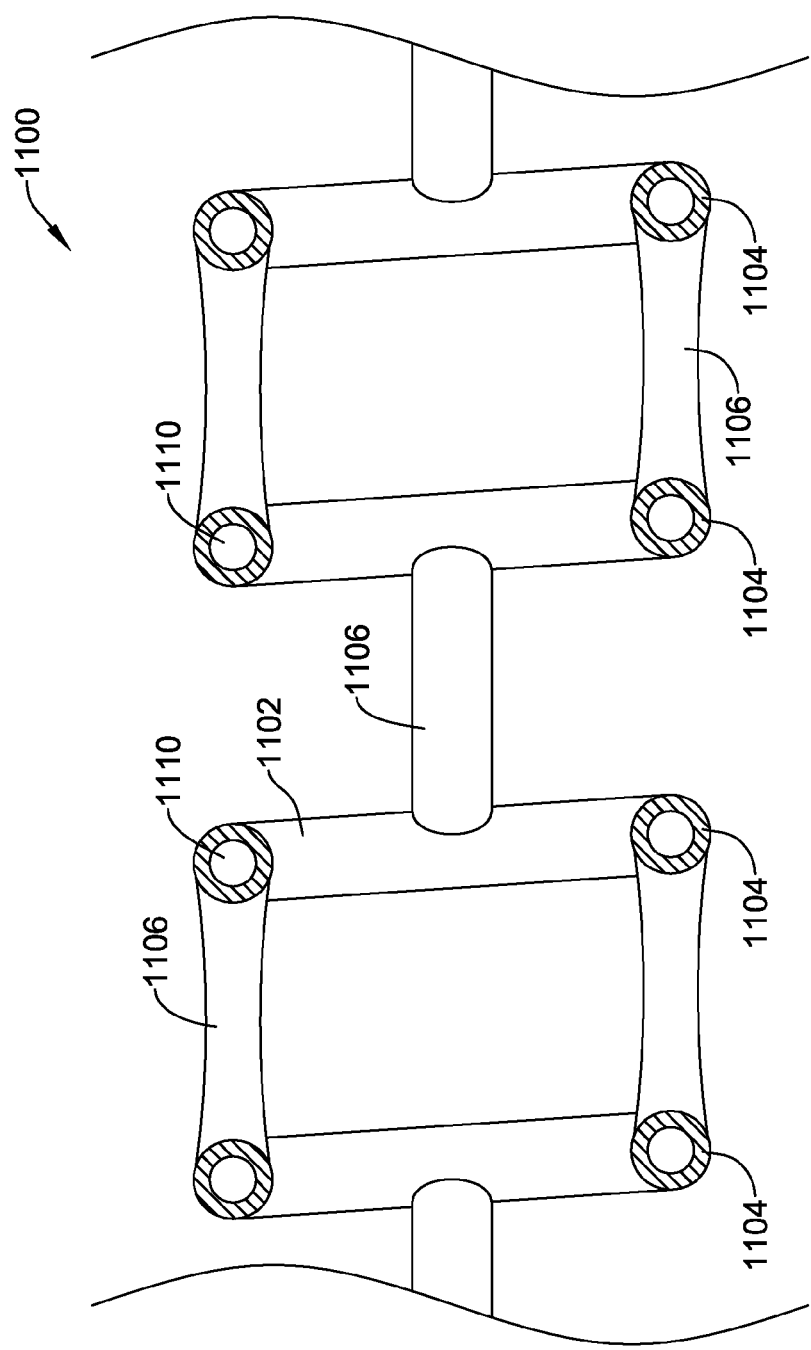
FIG. 13 is a cross-sectional view of another illustrative coil.

A cross-section of another coil 1100 taken along the longitudinal axis of the coil 1100 is shown in FIG. 13. The coil 1100, which may be a single filar coil, may be formed of a helically wound filament 1102, which in some embodiments may be a round wire or flat ribbon ranging in dimensions to achieve the desired flexibility. The coil 1100 is illustrated as a round wire coil. It can also be appreciated that other cross-sectional shapes or combinations of shapes may be utilized, as desired.

As shown in FIG. 13, adjacent coil windings or turns 1104 may be connected to each other at discrete locations. For example, adjacent coil turns 1104 may be welded or soldered to one another at discrete locations or welds 1106 along the length of the coil 1100. Welding or soldering adjacent coil turns 1104 at discrete locations or welds 1106 may enhance the flexibility and/or torsional properties of the coil 1100. For example, welding of adjacent coil turns 1104 may increase the torsional rigidity and torque transmitting properties of the coil 1100 without sacrificing the flexibility characteristics of the coil 1100. The welds 1106 between adjacent coil windings or turns 1104 may transfer torsional forces along the coil 1100 while the coil 1100 retains its flexibility. Thus, the coil 1100 may possess characteristics similar to those attributed to a slotted tubular member, such as a micromachined hypotube.

The pattern of welds 1106 of the coil 1100 may be any desired pattern, including those patterned expressly disclosed herein regarding other exemplary coils. Thus, in the interest of brevity, further discussion of possible weld patterns will not be provided.

As shown in FIG. 13, the filament 1102 may be a tubular filament having a lumen 1110 extending through the filament 1102. The lumen 1110 may provide a fluid pathway for the passage of fluid through a medical device. Thus, fluids may be delivered to the distal end of a medical device through the lumen 1110, or fluids may be drawn proximally through the lumen 1110 in some embodiments.

Figure 14:
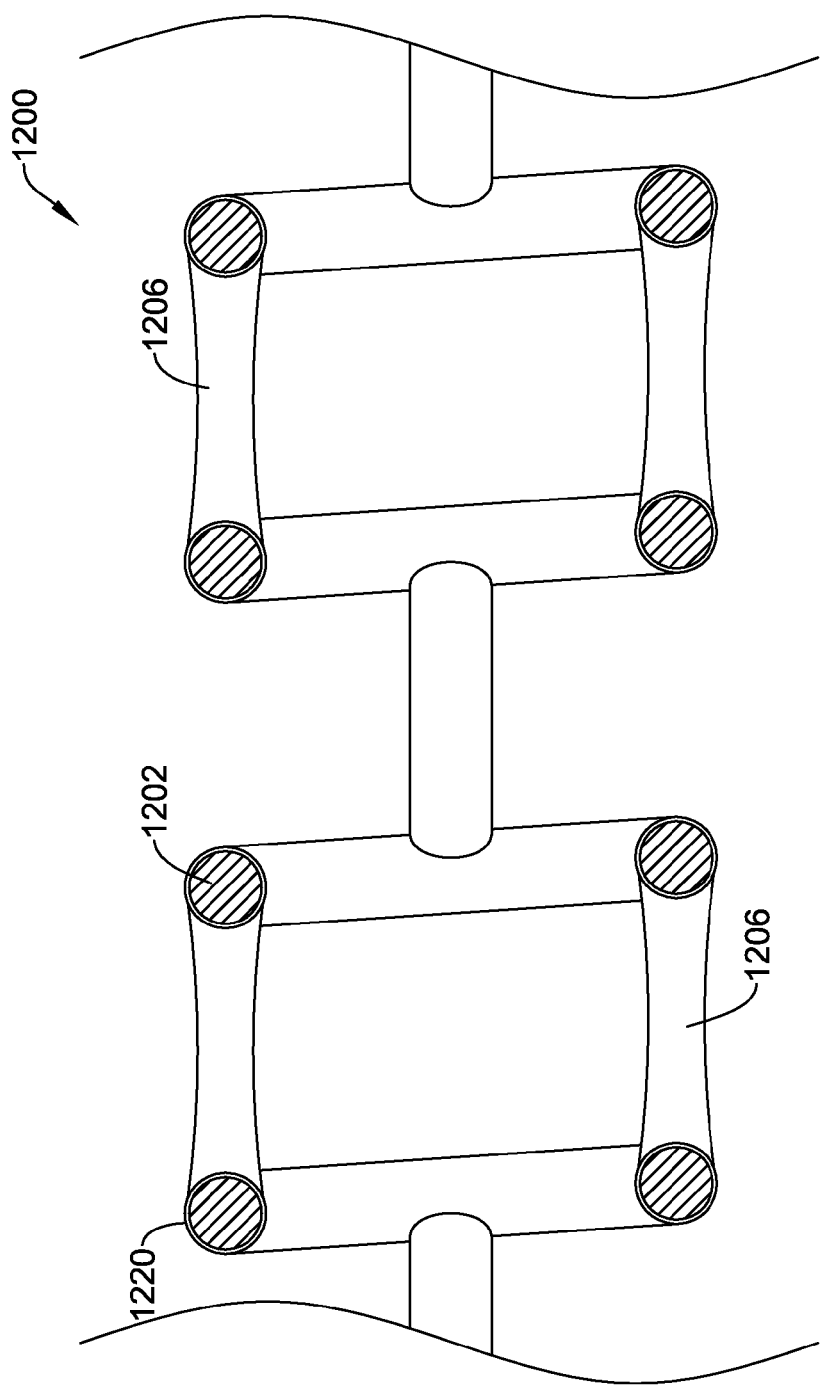
FIG. 14 is a cross-sectional view of yet another illustrative coil.
Figure 15A:
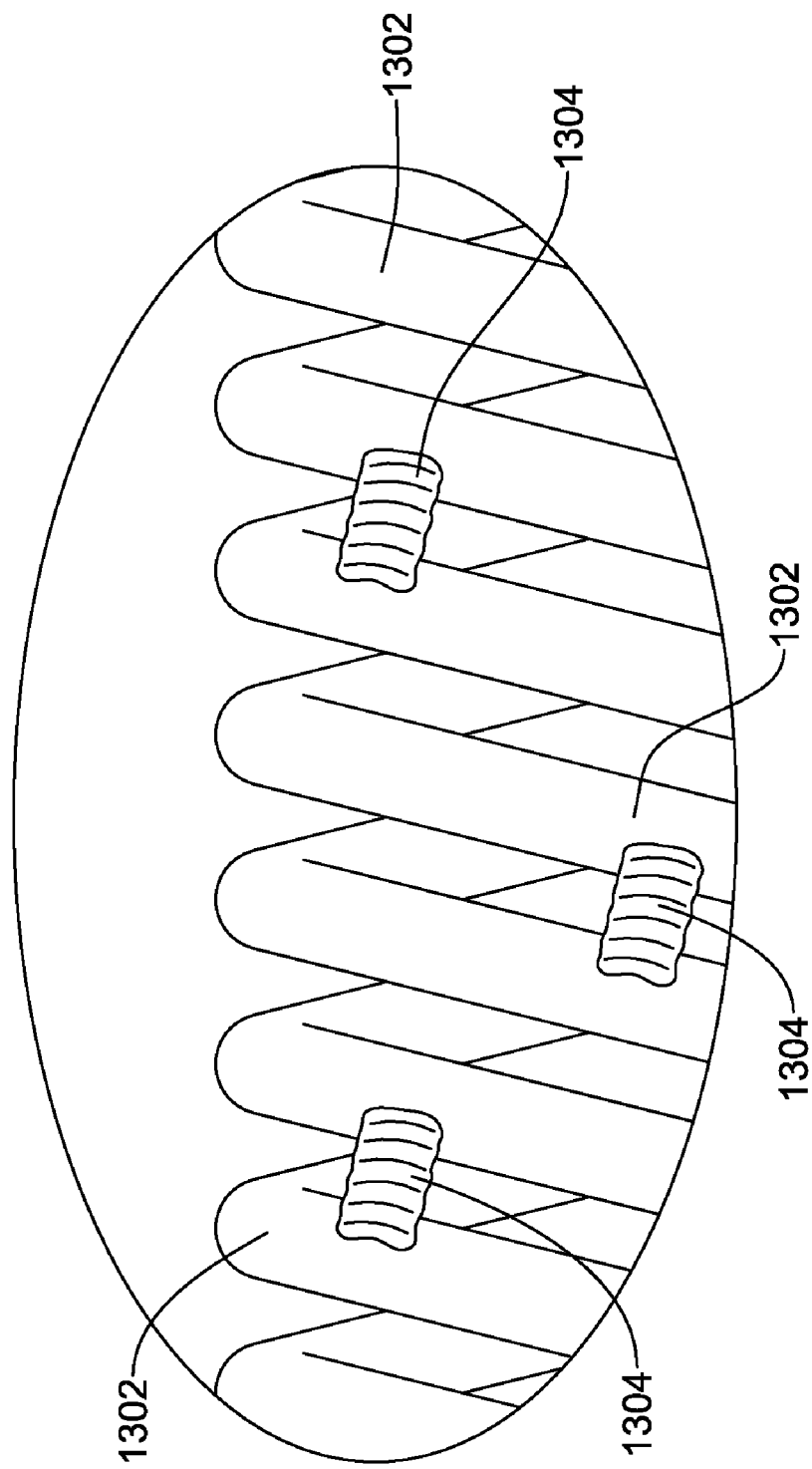
FIGS. 15A through 15C illustrate several possible variations of a weld welding adjacent windings of a coil together.
Figure 15B:
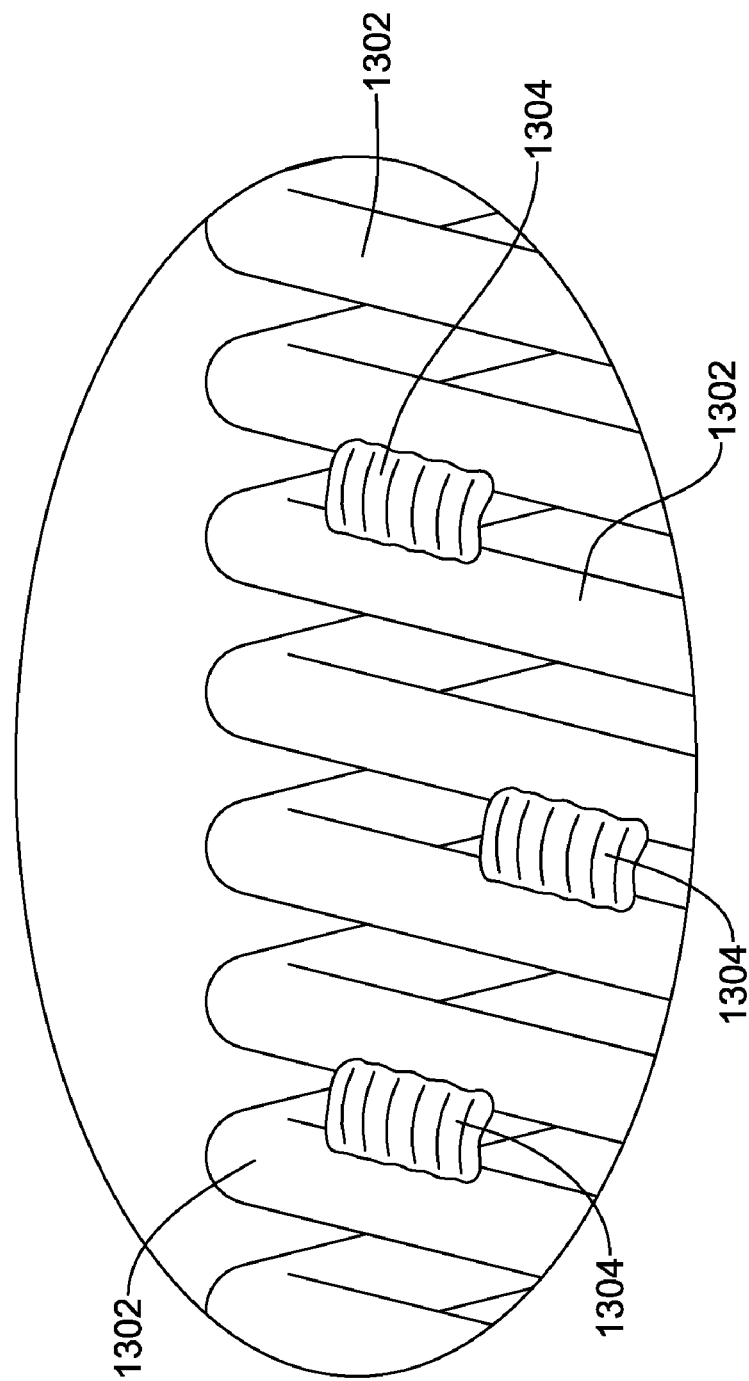
Figure 15C:
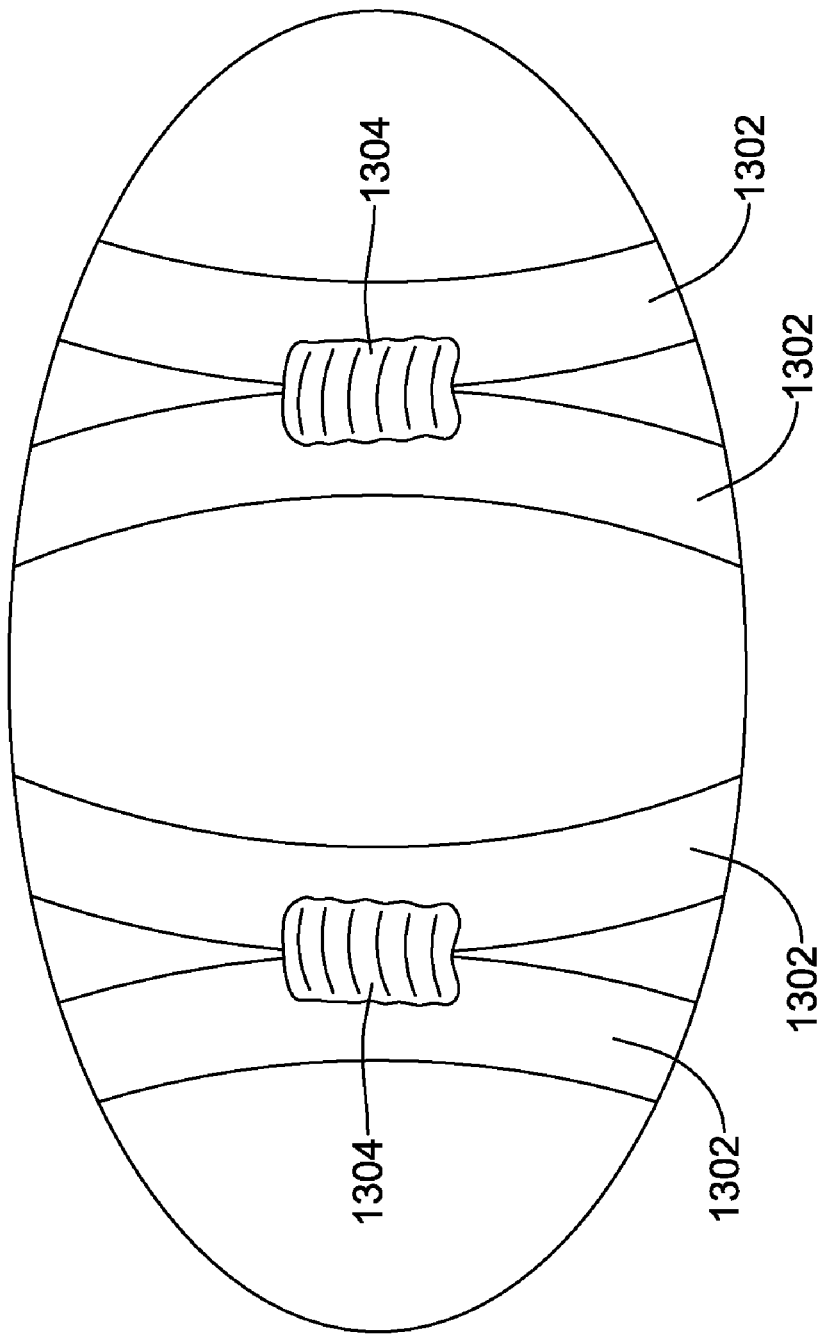

A cross-section of another coil 1200 taken along the longitudinal axis of the coil 1200 is shown in FIG. 14. The coil 1200, which may be a single filar coil, may be formed of a helically wound filament 1202, which in some embodiments may be a round wire or flat ribbon ranging in dimensions to achieve the desired flexibility. The coil 1200 is illustrated as a round wire coil. It can also be appreciated that other cross-sectional shapes or combinations of shapes may be utilized, as desired.

As shown in FIG. 14, the filament 1202 may include a coating 1220, such as a polymeric coating surrounding the filament 1202. In some embodiments, the coating 1220 may be an atraumatic coating, a hydrophilic coating, a hydrophobic coating, a drug eluting coating, or a insulative coating, for example. If an insulative coating is used to coat an electrically conductive filament, electricity may be conducted along the filament. The coating 1220 may be applied to the filament 1202 prior to being formed into a helical shape, or the coating 1220 may be applied after the coil 1200 has been put into its modified shape. If the coating 1220 is applied after the coil 1200 has been welded, the welds of the coil 1200 may additionally be coated with the coating 1200. It is noted that any of the coils disclosed herein may include such a coating, as desired.

As shown in FIG. 14, adjacent coil windings or turns 1204 may be connected to each other at discrete locations. For example, adjacent coil turns 1204 may be bonded to one another at discrete locations or bonds 1206 along the length of the coil 1200. In some embodiments, adjacent coil windings or turns 1204 may be connected with bonds 1206 by heating discrete areas of the polymer coating 1220 at or above the melting temperature of the polymer coating 1220 such that the molten polymer reflows to form the bonds 1206 between adjacent coil turns 1204. In other embodiments, bonds 1206 may be adhesive beads bonding adjacent coil turns 1204 together. In some embodiments, bonds 1206 may be welds securing adjacent coil turns 1204 together at discrete locations.

Bonding adjacent coil turns 1204 at discrete locations or bonds 1206 may enhance the flexibility and/or torsional properties of the coil 1200. For example, bonding of adjacent coil turns 1204 may increase the torsional rigidity and torque transmitting properties of the coil 1200 without sacrificing the flexibility characteristics of the coil 1200. The bonds 1206 between adjacent coil windings or turns 1204 may transfer torsional forces along the coil 1200 while the coil 1200 retains its flexibility. Thus, the coil 1200 may possess characteristics similar to those attributed to a slotted tubular member, such as a micromachined hypotube.

The pattern of bonds 1206 of the coil 1200 may be any desired pattern, including those patterns expressly disclosed herein regarding discrete connection locations of other exemplary coils. Thus, in the interest of brevity, further discussion of possible bond patterns will not be provided.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A medical device coil member comprising:
 a wave wound coil having a first end, a second end and a longitudinal axis extending between the first end and the second end, the wave wound coil formed of a filament wound about the longitudinal axis forming a plurality of turns;
 wherein each turn of the filament is a 360 degree revolution of the filament about the longitudinal axis;
 wherein each of the plurality of turns of the filament includes a wave pattern of two or more high periods and two or more low periods; and
 wherein adjacent turns of the filament are fixed together at two or more discrete locations along a length of the wave wound coil.

2. The medical device coil member of claim 1, wherein the wave pattern of each of the plurality of turns of the filament includes a plurality of crests and troughs, and wherein the crests of a first turn of the filament are fixed to the crests of a second turn of the filament.

3. The medical device coil member of claim 1, wherein the wave pattern of each of the plurality of turns of the filament includes two or more upper flat segments and two or more lower flat segments.

4. The medical device coil member of claim 3, wherein a length of the upper flat segments is less than a length of the lower flat segments of the wave pattern.

5. The medical device coil member of claim 3, wherein the upper flat segments of a first turn of the filament are fixed to the lower flat segments of a second turn of the filament.

6. The medical device coil member of claim 1, wherein the two or more high periods are momentary pulses extending from the low periods.

7. The medical device coil member of claim 1, wherein the high periods of a turn of the filament are phase shifted from the high periods of an immediately preceding turn of the filament.

8. The medical device coil member of claim 7, wherein the high periods of one turn of the filament are phase shifted about one half wavelength from the high periods of an immediately preceding turn of the filament.

9. The medical device coil member of claim 7, wherein the high periods of one turn of the filament are phase shifted about $1/36^{th}$ of a wavelength from the high periods of an immediately preceding turn of the filament.

10. A medical device coil member comprising:
 a wave wound coil including a plurality of coil windings helically wound about a longitudinal axis of the coil, wherein each coil winding is a 360 degree revolution of a filament of the wave wound coil;
 the wave wound coil including a first coil winding; a second coil winding immediately following the first coil winding, a third coil winding immediately following the second coil winding; and a fourth coil winding immediately following the third coil winding;
 wherein the second coil winding is welded to the first coil winding at two or more discrete locations, the third coil winding is welded to the second coil winding at two or more discrete locations, and the fourth coil winding is welded to the third coil winding at two or more discrete locations.

11. The medical device coil member of claim 10, wherein each coil winding includes two or more high periods and two or more low periods of a wave pattern; and wherein the high periods of the second coil winding are welded to the low periods of the first coil winding, the high periods of the third coil winding are welded to the low periods of the second coil winding, and the high periods of the fourth coil winding are welded to the low periods of the third coil winding.

12. The medical device coil member of claim 11, wherein the wave pattern of each coil winding includes two or more crests and the wave pattern of each coil winding includes two or more troughs.

13. The medical device coil member of claim 12, wherein the crests of the first coil winding are out of phase with the crests of the second coil winding.

14. The medical device coil member of claim 10, wherein the first coil winding is a non-waved coil winding, the second coil winding is a waved coil winding having a wave pattern, the third coil winding is a non-waved coil winding, and the fourth coil winding is a waved coil winding having a wave pattern.

15. The medical device coil member of claim 7, wherein the high periods of one turn of the filament are phase shifted about one quarter wavelength from the high periods of an immediately preceding turn of the filament.

16. A medical device including an elongate shaft, the elongate shaft comprising:

a wave wound coil extending along a portion of the elongate shaft;

the wave wound coil having a first end, a second end and a longitudinal axis extending between the first end and the second end, the wave wound coil formed of a filament wound about the longitudinal axis forming a plurality of turns;

wherein each turn of the filament is a 360 degree revolution of the filament about the longitudinal axis;

wherein each turn of the filament includes a wave pattern of two or more high periods and two or more low periods; and wherein each of the plurality of turns of the filament is welded to an immediately preceding turn of the filament at two or more discrete locations along a length of the wave wound coil.

17. The medical device of claim 16, wherein the wave pattern of each turn of the filament includes a plurality of crests and troughs, and wherein the crests of a first turn of the filament are welded to the crests of a second turn of the filament.

* * * * *